US012727900B2

(12) United States Patent
Toyoda et al.

(10) Patent No.: US 12,727,900 B2
(45) Date of Patent: Sep. 8, 2026

(54) ULTRASONIC HEAD DEVICE, ULTRASONIC THERAPY SYSTEM, AND METHOD FOR CONTROLLING ULTRASONIC THERAPY SYSTEM

(71) Applicants: HIRATA CORPORATION, Kumamoto (JP); SONIRE Therapeutics Inc., Tokyo (JP)

(72) Inventors: Kazutaka Toyoda, Kumamoto (JP); Yutaro Maruno, Kumamoto (JP); Takenori Hirakawa, Kumamoto (JP); Shinichi Matsunari, Kumamoto (JP); Jun Okamoto, Tokyo (JP)

(73) Assignees: HIRATA CORPORATION, Kumamoto (JP); SONIRE THERAPEUTICS INC., Tokyo (JP)

( * ) Notice: Subject to any disclaimer, the term of this patent is extended or adjusted under 35 U.S.C. 154(b) by 0 days.

(21) Appl. No.: 19/116,653

(22) PCT Filed: Sep. 29, 2022

(86) PCT No.: PCT/JP2022/036464
§ 371 (c)(1),
(2) Date: Mar. 28, 2025

(87) PCT Pub. No.: WO2024/069859
PCT Pub. Date: Apr. 4, 2024

(65) Prior Publication Data

US 2026/0102175 A1 Apr. 16, 2026

(51) Int. Cl.
*A61B 17/225* (2006.01)
*A61B 8/00* (2006.01)
(Continued)

(52) U.S. Cl.
CPC .......... *A61B 17/2251* (2013.01); *A61B 8/085* (2013.01); *A61B 8/4209* (2013.01);
(Continued)

(58) Field of Classification Search
CPC ..... A61B 8/085; A61B 8/4209; A61B 8/4281; A61B 8/4444; A61B 17/2255
See application file for complete search history.

(56) References Cited

U.S. PATENT DOCUMENTS

2019/0134430 A1 5/2019 Jeong

FOREIGN PATENT DOCUMENTS

JP 01091845 A 4/1989
JP 2000023990 A 1/2000
(Continued)

OTHER PUBLICATIONS

International Search Report (PCT/ISA/210) with translation and Written Opinion (PCT/ISA/237) mailed on Nov. 1, 2022, by the Japanese Patent Office as the International Searching Authority for International Application No. PCT/JP2022/036464. (10 pages).
(Continued)

*Primary Examiner* — Gerald Johnson
(74) *Attorney, Agent, or Firm* — Buchanan Ingersoll & Rooney PC

(57) ABSTRACT

Provided is an ultrasonic head device including: a base unit supported by a robot arm; a sonication unit which is provided on the base unit and includes a hemispherical sonication surface configured to radiate ultrasonic waves for sonication; a liquid bag which has a medium liquid through which the ultrasonic waves are transmitted accommodated therein and with which the sonication surface is covered; a liquid supplying and discharging unit which circulates the medium liquid through the liquid bag; and a moving mechanism which is provided on the base unit and supports the
(Continued)

liquid bag so that the liquid bag freely moves relative to the sonication surface along a direction of a central axis of the sonication surface.

11 Claims, 14 Drawing Sheets

(51) Int. Cl.

| | |
|---|---|
| ***A61B 8/08*** | (2006.01) |
| ***A61B 34/30*** | (2016.01) |
| *A61B 17/00* | (2006.01) |

(52) U.S. Cl.

CPC .......... *A61B 8/4281* (2013.01); *A61B 8/4444* (2013.01); *A61B 17/2255* (2013.01); *A61B 34/30* (2016.02); *A61B 2017/00477* (2013.01); *A61B 2017/2253* (2013.01)

(56) References Cited

FOREIGN PATENT DOCUMENTS

| | | | | |
|---|---|---|---|---|
| JP | 2020036709 | A | | 3/2020 |
| JP | 2020039397 | A | | 3/2020 |
| JP | 2021101510 | A | * | 7/2021 |
| WO | 2017200246 | A1 | | 11/2017 |

OTHER PUBLICATIONS

European Search Report dated Jun. 9, 2026, issued in corresponding European Patent Application No. 22960919.3 (10 pages).

* cited by examiner

ULTRASONIC HEAD DEVICE, ULTRASONIC THERAPY SYSTEM, AND METHOD FOR CONTROLLING ULTRASONIC THERAPY SYSTEM

TECHNICAL FIELD

The present invention relates to an ultrasonic head device which radiates ultrasonic waves for sonication to perform a therapy, an ultrasonic therapy system, and a method for controlling the ultrasonic therapy system.

BACKGROUND ART

There are known ultrasonic therapy devices having low invasive properties which perform a therapy such as cauterizing the affected parts such as cancer cells, tumors or the like in a patient's body by radiating ultrasonic waves to the affected parts, crushing stones or cells, and stimulating affected part or nerves (refer to, for example, Patent Document 1 and Patent Document 2). The ultrasonic therapy device described in Patent Document 1 includes a robot arm formed by joining a plurality of links using joints and an ultrasonic head device supported at a distal end of the robot arm and the ultrasonic head device includes a sonication unit having a sonication surface which sonicates an affected part with ultrasonic waves and a liquid bag which is filled with a medium liquid through which ultrasonic waves are transmitted provided between the sonication surface and a patient. Furthermore, the ultrasonic therapy device also includes a control unit using which the medium liquid is supplied and discharged to and from the liquid bag.

The ultrasonic waves radiated for sonication from the sonication unit of the ultrasonic therapy device described in Patent Document 1 have a focal point formed at a predetermined position away from the sonication surface. During a therapy, the ultrasonic head device is moved from a standby position to an appropriate position to have an appropriate posture by operating the robot arm in accordance with a position of an affected part so that a position of a focal point and a position of the affected part match. The liquid bag comes into contact with a patient's body surface and transmits ultrasonic waves to the affected part between the sonication surface and the patient's body surface. Thus, the inside of the liquid bag is filled with a medium liquid through which ultrasonic waves are transmitted.

The control unit adjusts an amount of medium liquid with which the liquid bag is filled by supplying and discharging the medium liquid to and from the liquid bag in accordance with a distance between the patient's body surface and the sonication surface. For example, when an affected part is located at a shallow position beneath the patient's body surface, the sonication surface needs to be moved away from the patient's body surface. Thus, the ultrasonic head device is held using the robot arm at a position in which it is away from the patient's body surface and an amount of medium liquid with which the liquid bag is filled is increased.

Also, when an affected part is located at a deep position beneath patient's body surface, the sonication surface needs to be close to the patient's body surface. Thus, the ultrasonic head device is held using the robot arm at a position in which it is close to the patient's body surface and an amount of medium liquid with which the liquid bag is filled is decreased. The ultrasonic head device described in Patent Document 2 includes a liquid bag having a bellows-like expandable and contractable structure and is constituted so that a position of a bottom surface of the liquid bag can be adjusted relative to the sonication surface by deforming the liquid bag in an upward/downward direction.

CITATION LIST

Patent Document

Patent Document 1: Japanese Unexamined Patent Application, First Publication No. 2020-036709

Patent Document 2: Japanese Unexamined Patent Application, First Publication No. H1-91845

SUMMARY OF INVENTION

Technical Problem

According to the ultrasonic therapy device described in Patent Document 1, when an amount of medium liquid is increased, there is a concern concerning that a liquid pressure in the liquid bag is increased, causing the liquid bag to rupture. Furthermore, according to the ultrasonic therapy device described in Patent Document 1, when an amount of medium liquid is reduced, there is a concern concerning that the liquid bag deflates and air gets trapped between the surface of the liquid bag and a patient's body surface during a therapy to form a gap therebetween so that ultrasonic waves cannot be appropriately transmitted to an affected part. There is a concern concerning that, when ultrasonic waves cannot be appropriately transmitted to an affected part, an unintended place is cauterized.

Since the liquid bag comes into direct contact with the patient's body surface, it is preferable to replace the liquid bag with a new one after each therapy from a hygiene management perspective. As the medium liquid which flows through the ultrasonic head device, for example, degassed water and the like are used. In degassed water, if an amount of air dissolved in the degassed water is increased or air bubbles are mixed into the degassed water, the transmission performance of ultrasonic waves decreases, resulting in a decrease in therapy accuracy. Thus, it is preferable to replace the degassed water with new degassed water after each therapy. That is to say, from a hygiene management and therapy accuracy perspective, replacing the liquid bag with a new one after each therapy, supplying unused degassed water to the replaced liquid bag while the air in the replaced liquid bag is discharged, filling an inside of the liquid bag with the degassed water, and then performing a therapy are required.

According to the ultrasonic head device described in Patent Document 2, since the liquid bag is constituted to have a bellows-like expandable and contractable structure, at the time of supplying degassed water into the liquid bag after subjecting the liquid bag to a replacement operation, there is a concern concerning that the air in the bellows part cannot be discharged and air bubbles are mixed into the medium liquid. When air bubbles are mixed into the medium liquid, there is a concern concerning that the air bubbles inhibit the transmission of ultrasonic waves, prevent the ultrasonic waves from being appropriately transmitted to an affected part to decrease therapy efficiency and increase a therapy time.

An object of the present invention is to provide an ultrasonic head device, an ultrasonic therapy system, and a method for controlling an ultrasonic therapy system in which, in order to appropriately transmit ultrasonic waves used for a therapy from a sonication instrument to an affected part, an amount of moisture of a medium liquid with which an inside of the liquid bag is filled and a liquid pressure thereof can be adjusted so that they are appropriately maintained in accordance with a depth of the affected part from a patient's body surface, the liquid bag can be easily replaced, and air bubbles can be prevented from getting mixed into the medium liquid when replacing the liquid bag or the medium liquid.

Solution to Problem

An aspect of the present invention is an ultrasonic head device supported by a robot arm which is able to be held in any posture state, the ultrasonic head device being applied to an ultrasonic therapy system which sonicates an inside of a therapeutic object with ultrasonic waves, the ultrasonic head device including: a base unit which is supported by the robot arm; a sonication unit which provided on the base unit and includes a hemispherical sonication surface configured to radiate the ultrasonic waves for sonication; a liquid bag which has a medium liquid through which the ultrasonic waves are transmitted accommodated therein and with which the sonication surface is covered; a liquid supplying and discharging unit which circulates the medium liquid through the liquid bag; and a moving mechanism which is provided on the base unit and supports the liquid bag so that the liquid bag can be freely moved relative to the sonication surface along a direction of a central axis of the sonication surface, in which the moving mechanism includes a first cylindrical unit which is provided on a side of the base unit, a second cylindrical unit which is provided to be freely moved relative to the first cylindrical unit along the direction of the central axis, and a first driving unit which moves the second cylindrical unit along the direction of the central axis, and the second cylindrical unit has the liquid bag fixed on a side which is different from the side of the base unit along the direction of the central axis.

Advantageous Effects of Invention

According to the present invention, it is possible to appropriately maintain an amount of moisture of a medium liquid with which an inside of a liquid bag is filled and a liquid pressure in accordance with a depth of an affected part from a patient's body surface.

BRIEF DESCRIPTION OF DRAWINGS

FIG. 4B A cross-sectional view showing a constitution of an ultrasonic head device.

FIG. 4C A diagram showing an operation of a moving mechanism.

DESCRIPTION OF EMBODIMENTS

Figure 1:
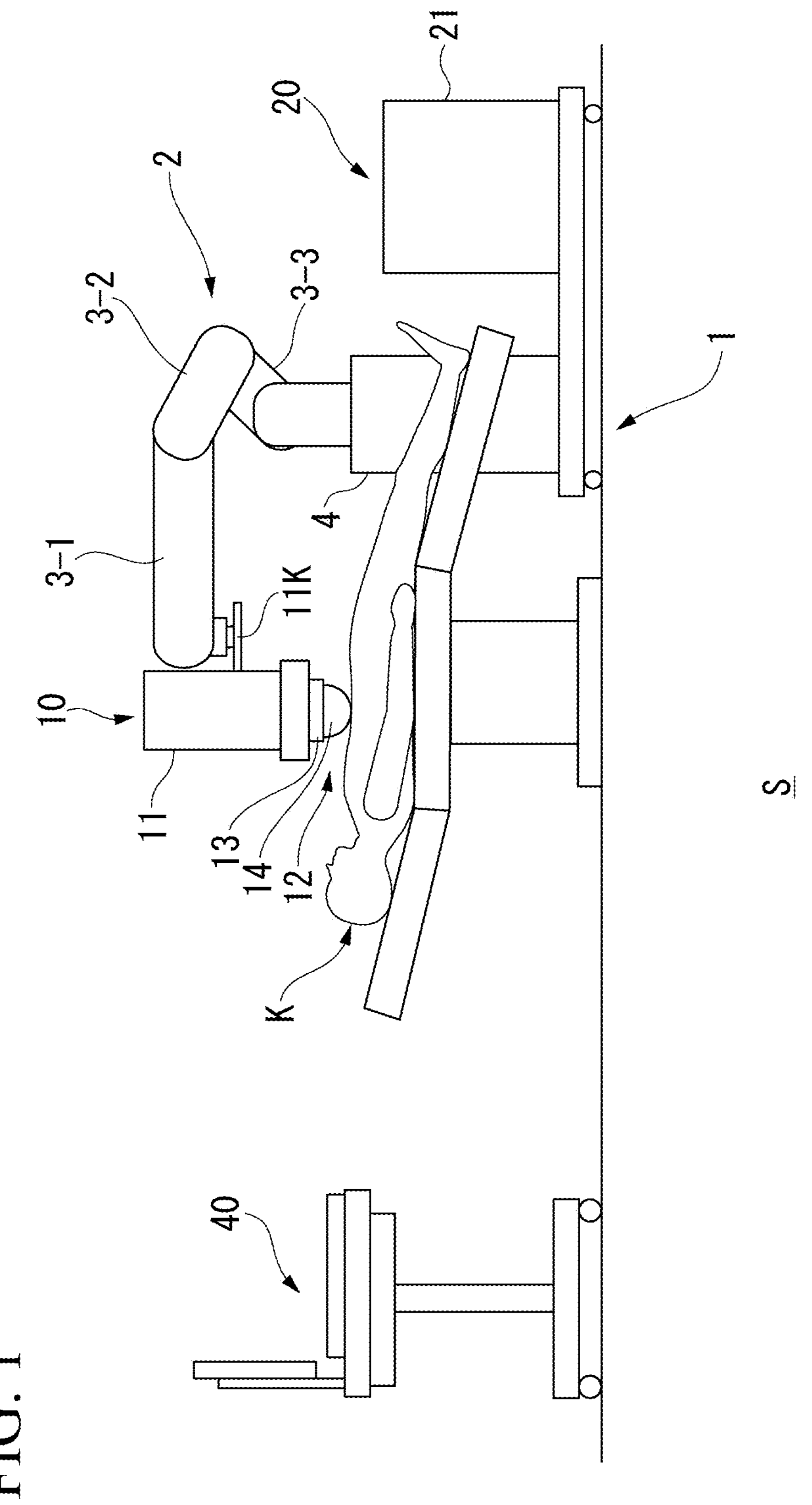
FIG. 1 A diagram showing a schematic constitution of an ultrasonic therapy system.
Figure 2:
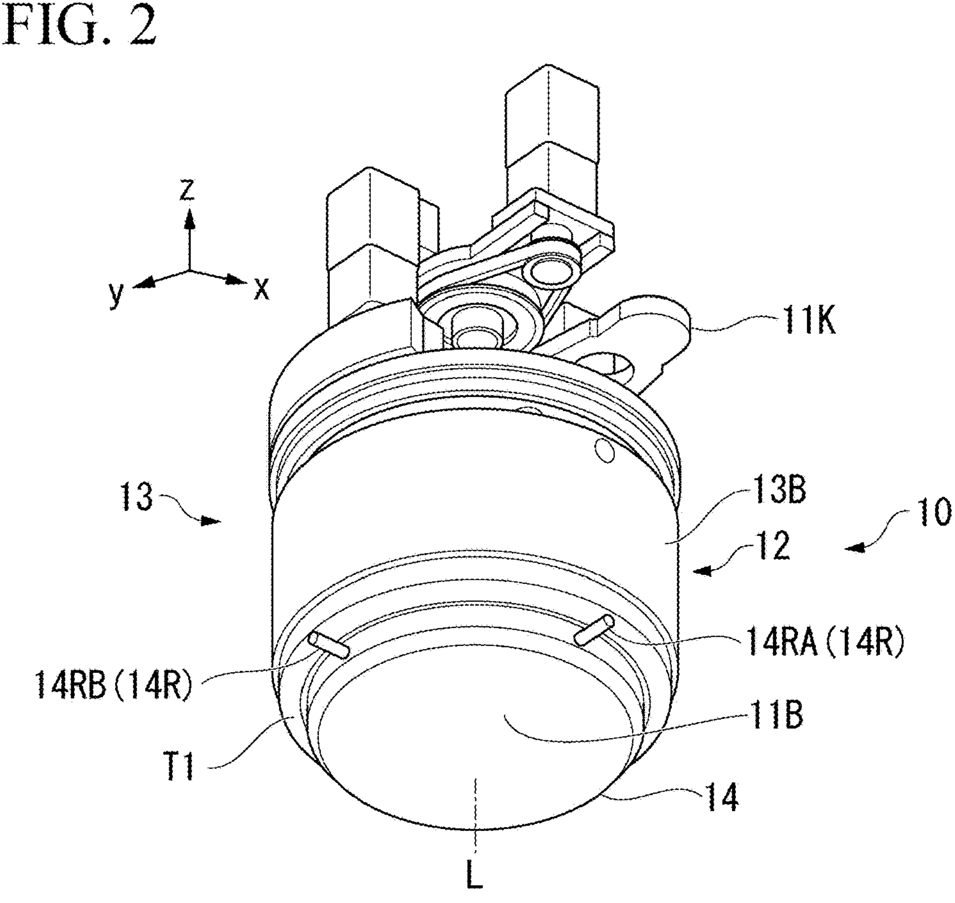
FIG. 2 A perspective view showing a constitution of an ultrasonic head device.
Figure 3:
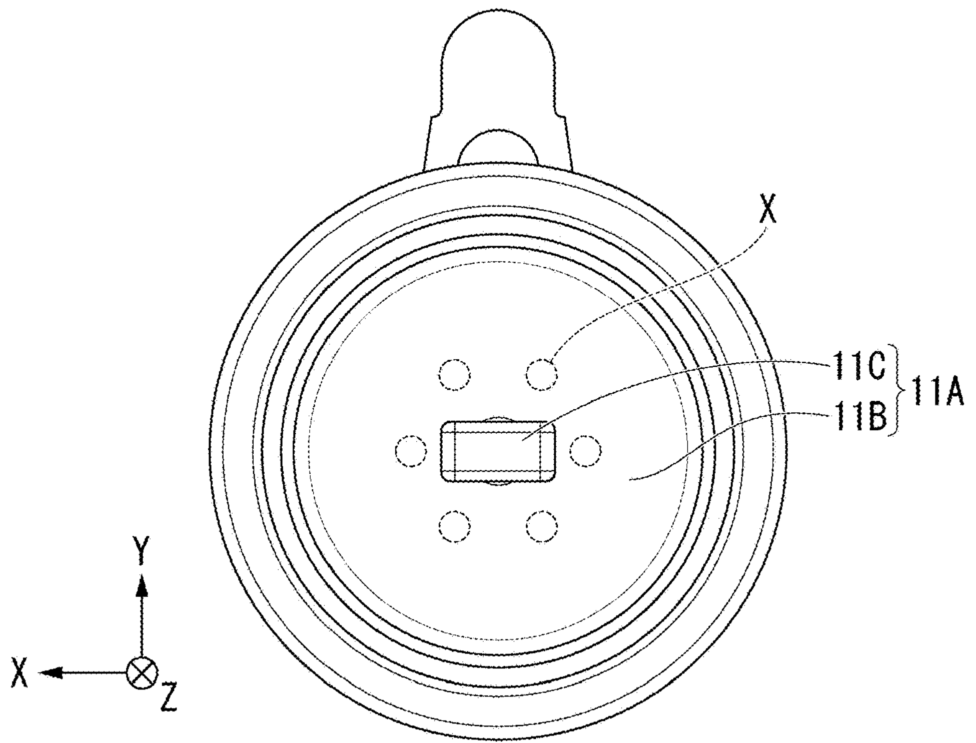
FIG. 3 A bottom surface diagram showing a constitution of the ultrasonic head device.

As shown in FIG. 1, an ultrasonic therapy system S includes an ultrasonic therapy device 1 which controls the sonication and a control device 40 which controls the ultrasonic therapy device 1 and manages a usage state and the like. The ultrasonic therapy device 1 includes a robot arm 2 which can support an object in any position and posture, an ultrasonic head device 10 which is provided at a distal end portion of the robot arm 2, a liquid storage unit 12 which is provided at a distal end portion of the ultrasonic head device 10 and is constituted to be able to adjust a volume, and a housing 20 which includes a fluid circuit unit 25 which circulates a medium liquid through the liquid storage unit 12 on the basis of a control command from the control device 40.

The robot arm 2 is constituted of, for example, a vertical multi-joint robot and the robot arm 2 is installed on a floor surface via an arm base 4. The robot arm 2 is constituted to be able to move the ultrasonic head device 10 to any position and to hold it in any posture state. The robot arm 2 can hold, for example, the ultrasonic head device 10 at a position in which the ultrasonic head device 10 comes into contact with a patient or hold the ultrasonic head device 10 at a position in which the ultrasonic head device 10 is away from the patient. Furthermore, the robot arm 2 can hold the ultrasonic head device 10, for example, in a posture in which a central axis L of the ultrasonic head device 10 extends in a vertical direction or in a position in which the central axis L is inclined from the vertical direction. Hereinafter, a direction along the central axis Lis referred to as "axial direction"or the like as appropriate.

The ultrasonic head device 10 sonicates an affected part of a patient K with ultrasonic waves and performs a therapy. Examples of the affected part include cancer cells such as liver cancer cells, and stones. The object for therapy based on ultrasonic waves may be animals as well people. The ultrasonic head device 10 includes an instrument which sonicates a therapeutic object with high intensity focused ultrasound (hereinafter referred to as an "HIFU") that is therapeutic ultrasonic waves and an instrument which radiates diagnostic ultrasound that is ultrasonic waves different from the HIFU for sonication and receives the diagnostic ultrasound.

As shown in FIGS. 2 to 4C, the ultrasonic head device 10 includes, for example, a sonication unit 11A which sonicates an affected part of a therapeutic object with ultrasonic waves at a lower end portion on an inner side of a main body part 11. The sonication unit 11A includes, for example, a first sonication unit 11B which generates a therapeutic HIFU and a second sonication unit 11C which is composed of a diagnostic probe configured to generate a diagnostic ultrasound.

The first sonication unit 11B is composed of, for example, a HIFU transducer which performs sonication with an HIFU so that a focal point X is generated. A lower surface side of the first sonication unit 11B includes a sonication surface 11B1 formed to have a dome shape and a plurality of ultrasonic oscillators (not shown) composed of piezoelectric elements or the like are aligned and disposed on an inner surface of the sonication surface 11B1. The plurality of ultrasonic oscillators are disposed such that the plurality of envelopes of the ultrasonic waves to be oscillated are focused at one or more focal points X. In the embodiment, six focal points X are generated on a plane orthogonal to the central axis L at positions at equal intervals about the central axis L. Here, the number of focal points X which are generated may be one. In that case, the focal point X is generated on the central axis L. The first sonication unit 11B may, for example, be disposed rotatably about the central axis L.

The second sonication unit 11C scans a therapeutic object with ultrasonic waves and generates cross-sectional images. For example, the second sonication unit 11C sonicates the patient K with a diagnostic ultrasound at a distal end portion and receives the diagnostic ultrasound reflected from an object such as an affected part of the patient K. The second sonication unit 11C protrudes downward from the sonication surface 11B1 of the first sonication unit 11B. The second sonication unit 11C radiates diagnostic ultrasound for sonication in a predetermined angle range with respect to the central axis L in the upward/downward direction and receives the reflected waves thereof. The second sonication unit 11C is rotatably installed along the central axis L. The second sonication unit 11C is provided to be movable in a direction along the central axis L.

The liquid storage unit 12 includes a liquid bag 14. The liquid bag 14 is formed to have a hemispherical shape in which it bulges downward. An internal space of the liquid bag 14 is filled with a medium liquid through which ultrasonic waves are transmitted as described below. The liquid bag 14 covers the sonication surface 11B1 of the first sonication unit 11B and the second sonication unit 11C protruding from the sonication surface 11B1. The sonication surface 11B1 and the second sonication unit 11C are immersed in the medium liquid with which the internal space of the liquid bag 14 is filled. An outside of a bottom portion of the liquid bag 14 comes into contact with a patient's body surface during diagnosis and during a therapy. The second sonication unit 11C is constituted to be rotatable and movable in the upward/downward direction in the internal space which is filled with a medium liquid. The distal end portion of the second sonication unit 11C, for example, comes into contact with an inside of the bottom portion of the liquid bag 14 during diagnosis. Thus, the second sonication unit 11C comes into contact with the patient K's body surface via the liquid bag 14 and diagnoses an inside of the patient K's body.

The liquid storage unit 12 is composed of, for example, a moving mechanism 13 which can be raised and lowered in a direction of the central axis L, the liquid bag 14, and an attachment unit T configured to attach the liquid bag 14 provided on a lower portion of the moving mechanism 13. The liquid storage unit 12 is constituted such that the volume of the internal space thereof filled with medium liquid can be adjusted using the moving mechanism 13. The liquid storage unit 12 has an internal space formed of, for example, the liquid bag 14, the moving mechanism 13, and the first sonication unit 11B. The internal space of the liquid storage unit 12 is filled with a medium liquid. The liquid bag 14 is constituted to be attachable to and detachable from the moving mechanism 13 and replaceable as described below.

The moving mechanism 13 is provided, for example, in a base unit 11K fixed to the main body part 11. The main body part 11 is supported by the robot arm 2 via the base unit 11K. The moving mechanism 13 is constituted to be able to freely elevate and lower the liquid bag 14 in the direction of the central axis L, thereby increasing or decreasing the volume of the internal space. The moving mechanism 13 includes, for example, a first cylindrical unit 13A provided on a side of the base unit 11K. The moving mechanism 13 includes a second cylindrical unit 13B which includes an attachment unit T having the liquid bag 14 attached to a lower side thereof. The second cylindrical unit 13B is held to be movable in the direction of the central axis L. The moving mechanism 13 includes a movement driving unit which moves the second cylindrical unit 13B in the direction of the central axis L relative to the first cylindrical unit 13A. A movement driving unit is composed of a third cylindrical unit 13C and a first driving unit C described later.

The first cylindrical unit 13A is formed to have, for example, a cylindrical shape about the central axis L. A plurality of first groove portions 13A2 are formed in an outer circumferential surface 13A1 of the first cylindrical unit 13A. The first groove portions 13A2 are formed to have a linear groove shape in which the first groove portions 13A2 extend in the direction of the central axis L. Three first groove portions 13A2 are formed, for example, at three positions evenly spaced in a circumferential direction of the outer circumferential surface 13A1. The first groove portions 13A2 are formed to have, for example, a linear groove shape in which the first groove portions 13A2 have a predetermined length from an end portion on an upper side of the first cylindrical unit 13A. The first groove portions 13A2 are formed to have a groove shape in which the first groove portions 13A2 have a predetermined depth from a side of the outer circumferential surface 13A1. A region of the outer circumferential surface 13A1 below a lower end of the first groove portion 13A2 is a sliding region 13A3 on which a sealing member S1 described later slides. The first cylindrical unit 13A is inserted into the second cylindrical unit 13B and an outer circumferential surface Al of the first cylindrical unit 13A faces an inner circumferential surface 13B2 of the second cylindrical unit 13B described later.

The second cylindrical unit 13B is formed to have, for example, a cylindrical shape about the central axis L. The second cylindrical unit 13B includes one or more through holes 13BH formed to pass through the second cylindrical unit 13B from an outer circumferential surface 13B1 to an inner circumferential surface 13B2. The through holes 13BH are provided at positions in which the through holes 13BH correspond to the first groove portions 13A2 of the first cylindrical unit 13A and are formed, for example, at three positions evenly spaced about the central axis L. Engagement members 13BP are inserted into three through holes 13BH, respectively. The engagement members 13BP are formed to be cylindrical pin members. The engagement members 13BP are respectively provided to protrude in the radial direction from the side of the inner circumferential surface 13B2 toward the central axis. The engagement members 13BP are formed to be engaged with the first groove portions 13A2 when the first cylindrical unit 13A is inserted into the second cylindrical unit 13B. The distal end portion of the engagement member 13BP is guided into the first groove portion 13A2 and slides along the first groove portion 13A2. One of the first cylindrical unit 13A and the second cylindrical unit 13B includes one or more first groove portions 13A2 formed along the direction of the central axis. The other of the first cylindrical unit 13A and the second cylindrical unit 13B includes one or more engagement members 13BP which protrude in a radial direction and are formed to be engaged with the first groove portions 13A2. A distal end portion of each of the engagement members 13BP may have a roller (not shown) provided to run along the first groove portion 13A2. In the embodiment, an engagement unit is constituted of three engagement members 13BP. The engagement member 13BP are guided into the first groove portions 13A2 so that the second cylindrical unit 13B is provided movably along the direction of the central axis L relative to the first cylindrical unit 13A. The second cylindrical unit 13B moves within a predetermined range of an amount of movement along the axial direction on the basis of, for example, the rotation of a third cylindrical unit 13C described later. The third cylindrical unit 13C is rotationally driven using the first driving unit C.

A sealing groove portion 13BM into which a sealing member S1 is fitted is formed in a lower portion of the inner circumferential surface 13B2 of the second cylindrical unit 13B. The sealing groove portion 13BM is provided, for example, on the lower portion of the inner circumferential surface 13B2 along the circumferential direction about the central axis L. The sealing groove portion 13BM is provided to extend along the circumferential direction of the inner circumferential surface 13B2. A sealing member S1 formed to have an annular shape which seals a gap between the sealing groove portion 13BM and the sliding region 13A3 on the outer circumferential surface 13A1 of the first cylindrical unit 13A is fitted into the sealing groove portion 13BM. One or more sealing groove portions 13BM and sealing members S1 may be provided to be separated in the axial direction. A sealing unit is constituted of the sealing groove portions 13BM and the sealing members S1. The sealing unit is formed along the circumferential direction centering on the central axis L and seals a gap between the inner circumferential surface 13B2 of the second cylindrical unit 13B and the sliding region 13A3 of the outer circumferential surface 13A1 of the first cylindrical unit 13A to ensure watertightness therebetween.

The attachment unit T (refer to FIG. 2) to which the liquid bag 14 can be attached in an attachable and detachable manner is provided on the outer circumferential surface 13B1 of the second cylindrical unit 13B. The attachment unit T includes, for example, a plurality of buckles (not shown in the drawings) provided to be spaced evenly along the circumferential direction of the outer circumferential surface 13B1 and an annular member T1 fixed using the plurality of buckles. The buckles are formed so that the annular member T1 can be attached and detached on the basis of, for example, a lever operation. The annular member T1 is provided to be openable and closable with respect to the second cylindrical unit 13B via, for example, a hinge structure (not shown).

An end surface 13BT of a lower end portion of the second cylindrical unit 13B is formed to have an annular shape in which it has a predetermined width. A flange unit 14C described later provided at an upper end of the liquid bag 14 comes into contact with the end surface 13BT. If the annular member T2 is set in the flange unit 14C and the attachment unit T comes to be in a closed state by operating the buckles, the annular member T2 is engaged with the flange unit 14C and cooperates with an end surface 13BT of the lower end portion of the second cylindrical unit 13B so that the annular member T2 and the end surface 13BT have the flange unit 14C placed therebetween.

With the above constitution, the annular member T2 cooperates with the attachment unit to make the liquid bag 14 detachable and also adheres a flange unit 14C. of the liquid bag 14 to an end surface 13BT of the lower end portion of the second cylindrical unit 13B, thereby ensuring watertightness between the second cylindrical unit 13B and the liquid bag 14.

The movement driving unit includes the third cylindrical unit 13C and the first driving unit C described later which rotationally drives the third cylindrical unit 13C. The third cylindrical unit 13C is supported to be freely rotatable about the central axis L and a part of the third cylindrical unit 13C is inserted into a gap between an inner circumferential surface 13B2 of the second cylindrical unit 13B and an outer circumferential surface 13A1 of the first cylindrical unit 13A. The third cylindrical unit 13C includes, for example, a circular ring member 13C1 formed to have an annular shape and a cylindrical unit 13C2 formed to hang down downward from the circular ring member 13C1. A flange unit 13CF which protrudes in the radial direction centering on the central axis L is formed to extend at an upper end of the circular ring member 13C1. The flange unit 13CF comes into contact with an upper end of the first cylindrical unit 13A.

The cylindrical unit 13C2 is inserted into a gap formed between an inner circumferential surface 13B2 of the second cylindrical unit 13B and an outer circumferential surface 13A1 of the first cylindrical unit 13A. Second groove portions 13CM inclined with respect to the direction of the central axis and extending in the circumferential direction with respect to the central axis are formed to pass through the cylindrical unit 13C2. The second groove 13CM are formed, for example, in a length of one circumference or less of a spiral track with predetermined pitch intervals therebetween around a predetermined direction centering on the central axis L. The engagement members 13BP (engagement unit) provided at the second cylindrical unit 13B respectively pass through the second groove portions 13CM. An upper end side of the second groove portion 13CM is, for example, a start point of the second groove portion 13CM. A lower end side of the second groove portion 13 CM is, for example, an end point of the second groove portion 13 CM.

Figure 4A:
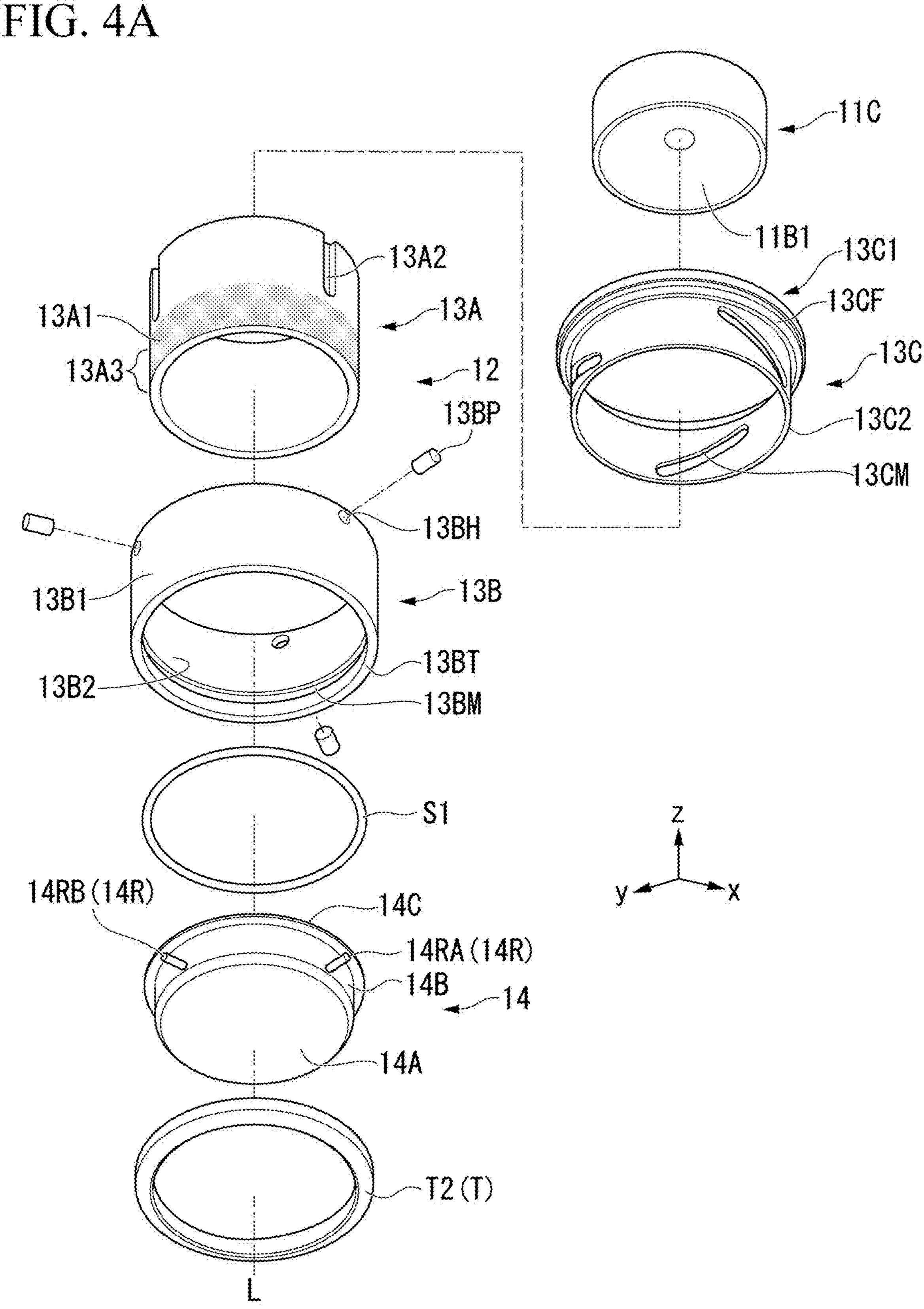
FIG. 4A An exploded perspective view showing a constitution of a moving mechanism.
Figure 4B:
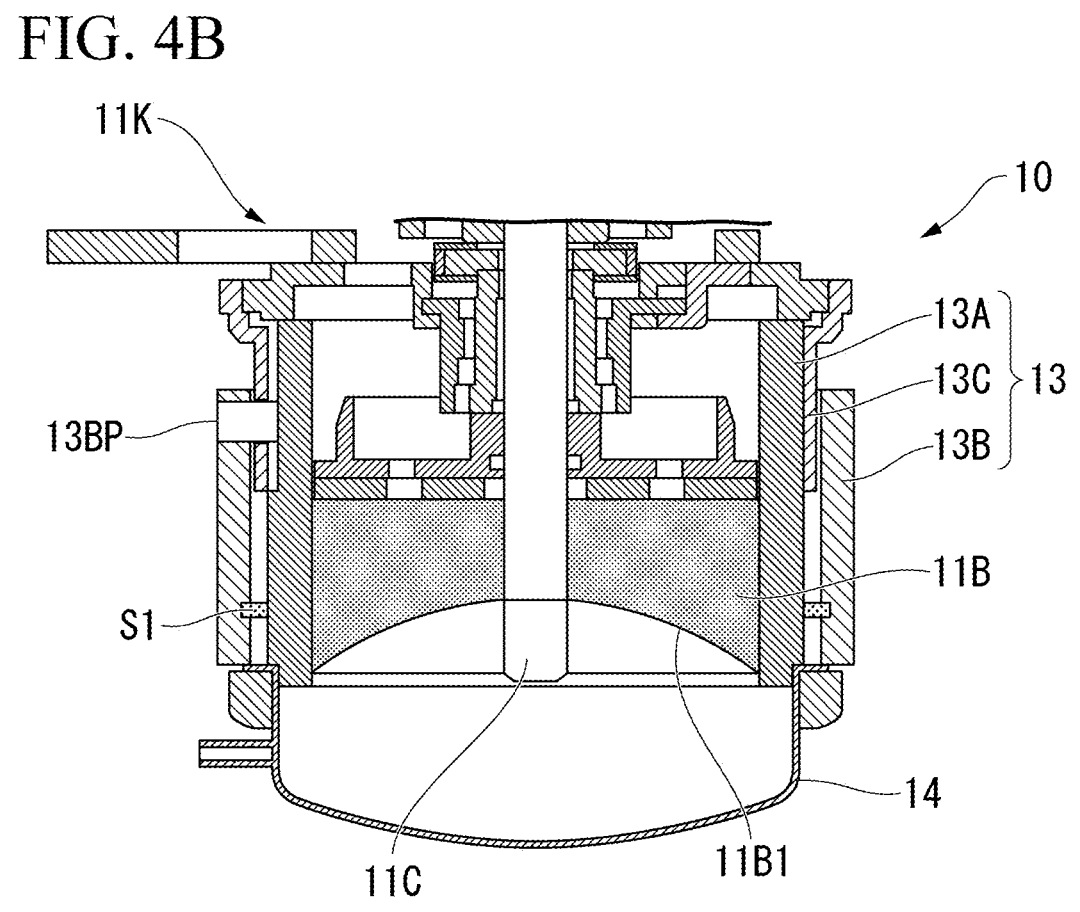
Figure 4C:
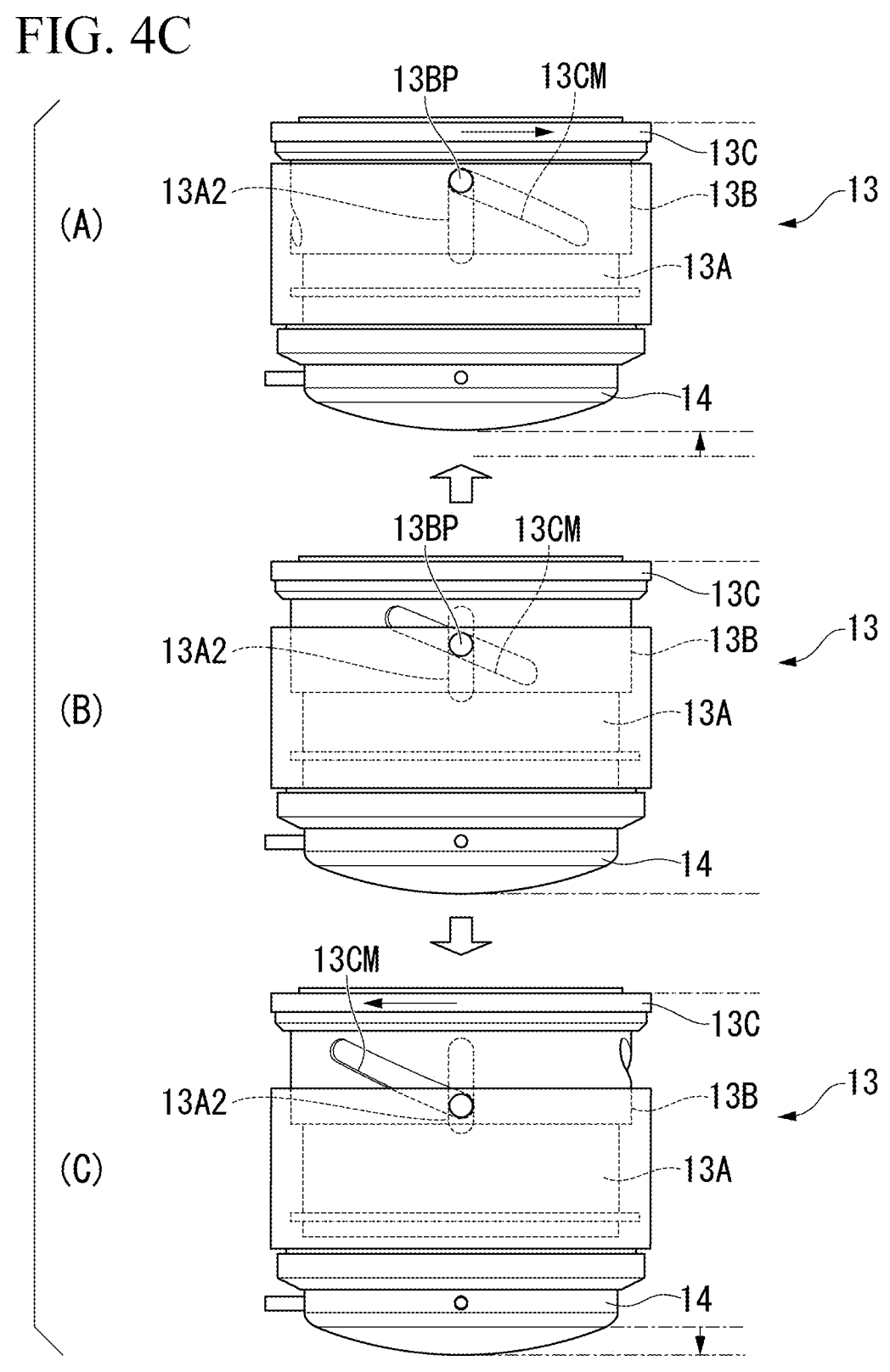

FIG. 4C(B) shows an initial state (or standby state) of the ultrasonic head device 10 before an operator operates the ultrasonic therapy system S for a therapy. The engagement members 13BP are located near the middle of the first groove portions 13A2 and the second groove portion 13CM. Here, when the third cylindrical unit 13C rotates from the initial state in the right direction in the drawing (counterclockwise when viewed in a plane view) as shown in FIG. 4C(A), as the second groove portion 13CM moves in the right direction, the engagement members 13BP rise following the first groove portions 13A2. As the engagement members 13BP rise, the second cylindrical unit 13B also rises. Through this operation, the liquid bag 14 approaches the sonication surface 11B1 and the volume of the internal space of the liquid storage unit 12 decreases. Here, when the third cylindrical unit 13C rotates from the initial state in the left direction in the drawing as shown in FIG. 4C(C) (clockwise when viewed in a plane view), as the second groove portion 13CM moves in the left direction, the engagement members 13BP are lowered following the first groove portions 13A2. As the engagement members 13BP are lowered, the second cylindrical unit 13B is also lowered. Through this operation, the liquid bag 14 moves away from the sonication surface 11B1 and the volume of the internal space of the liquid storage unit 12 increases.

With the above constitution, the second cylindrical unit 13B is movable by any amount of movement in the axial direction within the range in which the engagement members 13BP are guided by the second groove portions 13CM and the first groove portions 13A2. Furthermore, by reducing an inclination angle between a plane which is orthogonal to the central axis L and the second groove portion 13CM, it is possible to reduce a force required for a first driving unit C described later to rotate the third cylindrical unit 13C. Thus, it is possible to reduce a driving source used for the first driving unit C and it is possible to reduce a size of a device constitution.

Also, although the engagement member is located near the middle of the second groove portion in the initial state in the embodiment, for example, in the initial state, the engagement member may be located at the start point (upper end) or the end point (lower end) of the second groove portion.

That is to say, third cylindrical unit 13C can be rotated and driven in the circumferential direction centering on the central axis L relative to the first cylindrical unit 13A and the second cylindrical unit 13B by the first driving unit C described later to move the engagement members 13BP along the second groove portions 13CM and the first groove portions 13A2 and move the second cylindrical unit relative to the first cylindrical unit by any amount of movement in the axial direction of the central axis L on the basis of the rotation direction.

The liquid bag 14 is formed, for example, in a bowl shape in which it bulges downward. The liquid bag 14 is made of a material which has biocompatibility and has an acoustic impedance similar to that of a living body. The liquid bag 14 is made of a flexible material such as silicone rubber. The liquid bag 14 is constituted to be replaceable for each therapy. A contact part 14A which comes into contact with the patient K's body is formed on a side of the lower surface of the liquid bag 14. The contact part 14A is formed to have a semi-spherical tray shape. Around the contact part 14A, a cylindrical circumferential wall part 14B is formed of which a lower portion is continuous with the contact part and which extends to surround the upper part of the circumference of the contact part. The circumferential wall part 14B is formed to have, for example, a truncated cone shape in which a diameter thereof increases toward an upper side. The circumferential wall part 14B is installed in an installation target portion (not shown in the drawing) of the ultrasonic head device 10. A flange unit 14C. which is engaged with the installation target portion is formed at an upper end of the circumferential wall part 14B. The flange unit 14C is formed to have an annular shape protruding outward in the horizontal direction.

A liquid supplying and discharging unit 14R which circulates a medium liquid through the liquid bag via the fluid circuit unit 25 is provided on the circumferential wall part 14B. The liquid supplying and discharging unit 14R includes an inflow connection unit 14RA through which the medium liquid flows in from the fluid circuit unit 25 and a discharge connection unit 14RB through which the medium liquid is discharged from the liquid bag 14. An inflow connection unit 14RA is provided at a first position on the circumferential wall part 14B. The inflow connection unit 14RA is connected to a flow path of the fluid circuit unit 25. When viewed in a plane view, a discharge connection unit 14RB is provided at a second position different from the first position on the circumferential wall part 14B. The second position is, for example, a position spaced 90 degrees to the first position about a center of the contact part 14A relative when viewed in a plane view. The discharge connection unit 14RB is connected to a flow path of the fluid circuit unit 25.

Figure 5:
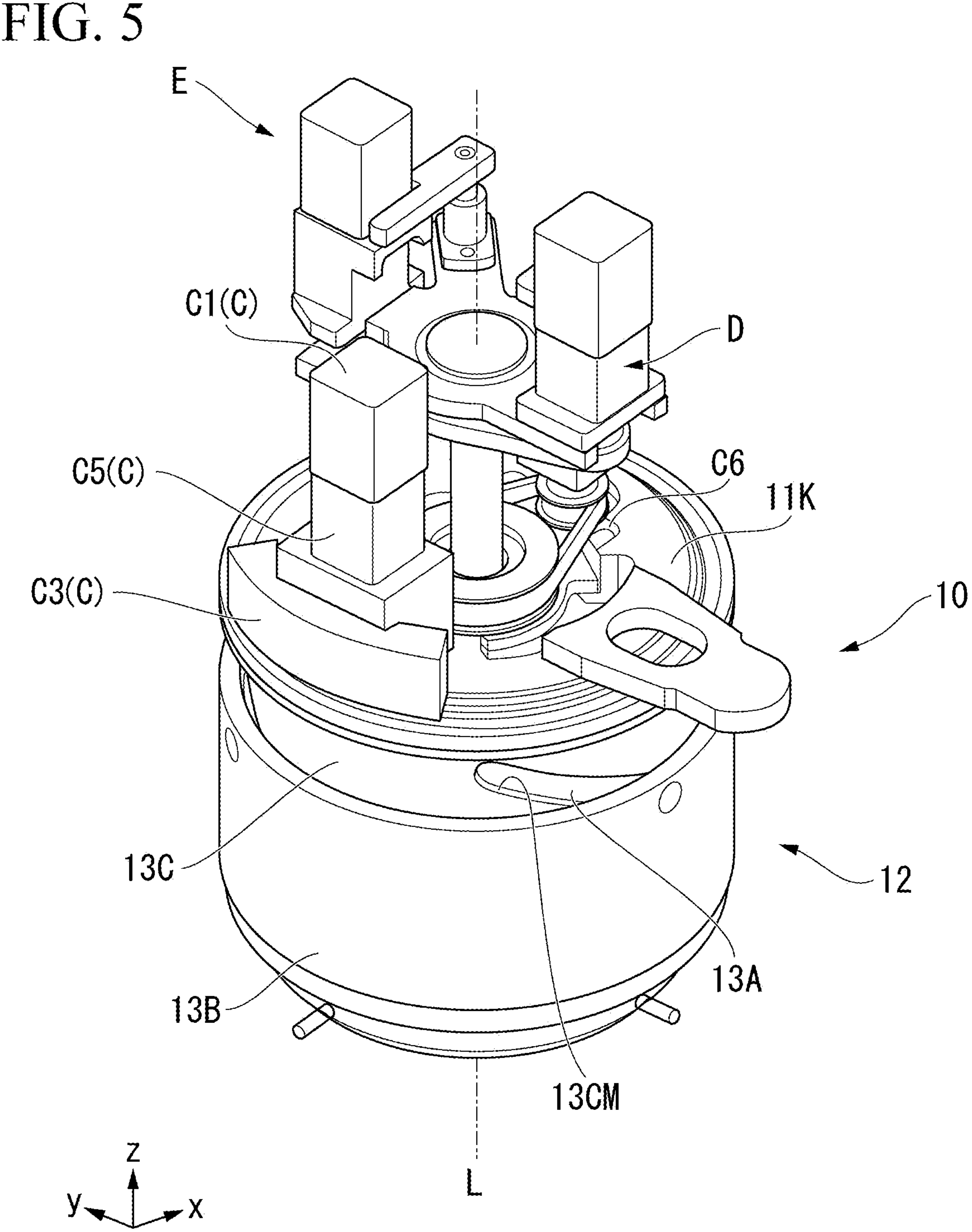
FIG. 5 A perspective view showing a constitution of a first driving unit.

FIG. 5 shows an internal structure of the main body part 11 of the ultrasonic head device 10. The third cylindrical unit 13C is rotationally driven about the central axis L using the first driving unit C. The first driving unit C is composed of, for example, a first motor which serves as a driving source C1, a first gear (not shown in the drawings) which is rotationally driven by the first motor, and a second gear C3 which meshes with the first gear. Between the first motor and the first gear, a speed reducer C5 which reduces the rotation speed of the first motor and increases the torque of the rotation output is provided. If the first motor has sufficient torque, the speed reducer C5 does not necessarily need to be provided.

The first motor includes a rotation shaft (not shown in the drawings) along the central axis L and the first gear is provided below the rotation shaft. The first gear is, for example, a pinion gear. The first motor is fixed via a fixture member C6 to a base unit 11K which fixes a part of the first motor on the first cylindrical unit 13A side. The first motor transmits rotational power to the second gear C3 via the first gear. The second gear C3 is formed, for example, as an internal gear (rack gear) which has an outer diameter having the same diameter as an outer diameter of the first cylindrical unit 13A. The second gear C3 is formed by cutting out a part of the internal gear within a predetermined angle range which has the central axis L as a center thereof. The second gear C3 is formed such that the engagement member 13BP described above is formed within a predetermined angle range in which it can move relatively along the second groove portion 13CM from a terminal end to a start end of the second groove portion 13CM. The second gear C3 is, for example, screwed to an upper end of the third cylindrical unit 13C via the base unit 11K.

With the above constitution, when the first gear serving as an output unit C2 is rotationally driven by the first motor, a driving force is transmitted to the second gear C3 and the third cylindrical unit 13C is rotationally driven about the central axis L via the second gear C3. When the third cylindrical unit 13C is rotationally driven by the first motor, the second cylindrical unit 13B moves by any amount of movement within a predetermined range along the axial direction relative to the first cylindrical unit 13A. As described above, the liquid bag 14 is formed to have a bowl shape in which it bulges downward and the moving mechanism 13 is constituted to move the second cylindrical unit 13B and the liquid bag 14 which is attached to the lower portion of the second cylindrical unit 13B relative to the first cylindrical unit 13A. For this reason, compared to when the liquid bag 14 has a bellows-like expandable and contractable structure, it is possible to prevent air bubbles from getting mixed in when filling the internal space of the liquid storage unit 12 with a medium liquid after replacing the liquid bag 14.

Figure 6:
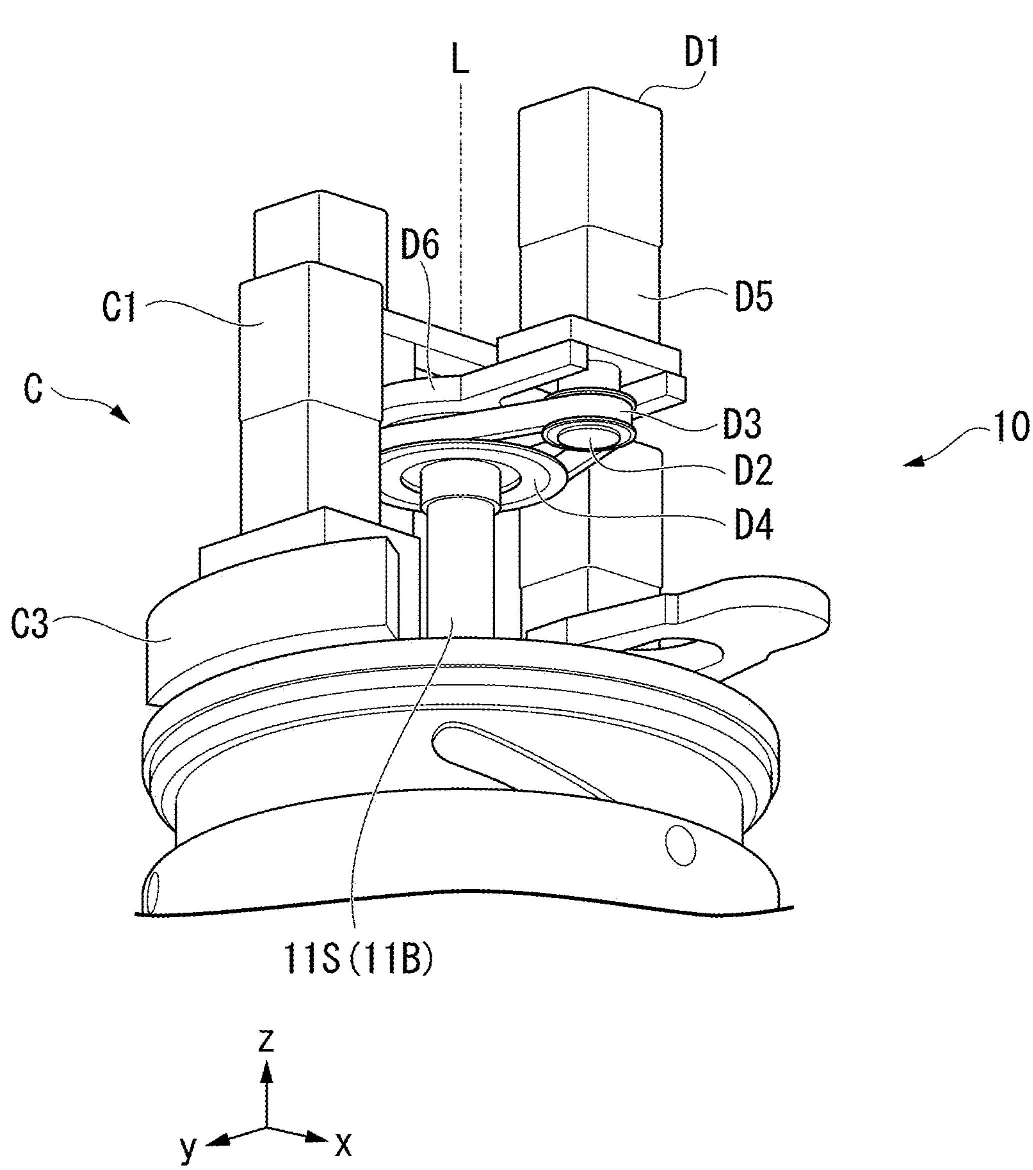
FIG. 6 A perspective view showing a constitution of a second driving unit.

As shown in FIG. 6, the second sonication unit 11C (refer to FIG. 4B) is rotationally driven by a second driving unit D about the central axis L. The second driving unit D is composed of, for example, a second motor D1 serving as a driving source, a first pulley D2 which is rotationally driven by the second motor D1, a first belt D3 which transmits a rotational power of the first pulley D2, and a second pulley D4 which is rotationally driven by the first belt D3. A speed reducer D5 which reduces a rotation speed of the second motor D1 and increases the torque of a rotation output is provided between the second motor D1 and the first pulley D2. If the torque of the second motor D1 is sufficiently ensured, the speed reducer D5 does not necessarily need to be provided. The second motor D1 includes a rotation shaft (not shown in the drawings) along a central axis L and the first pulley D2 is provided below the rotation shaft.

For example, the first belt D3 is fitted to the first pulley D2. The second pulley D4 is formed to have a diameter larger than that of the first pulley D2. The first belt D3 is fitted to the second pulley D4. A shaft 11S which is joined to a second sonication unit 11C (refer to FIG. 2) is concentrically connected to the second pulley D4. The shaft 11S extends above the second sonication unit 11C. A second sonication unit 11C is provided at a lower end portion of the shaft 11S. The shaft 11S is supported by the base unit 11K to be rotatable about the central axis L and is supported to be movable along the direction of the central axis L.

The second pulley D4 increases the torque of a rotation output of the first pulley D2 and rotationally drives the second sonication unit 11C through the shaft 11S. The second motor D1 is fixed via a support member D6. The support member D6 regulates the movement in the circumferential direction of the second motor D1 about the central axis L. The support member D6 moves along the direction of the central axis L as described below. With the above constitution, when the first pulley D2 is rotationally driven by the second motor D1, the second pulley D4 is rotated via the first belt D3 and the second sonication unit 11C is rotationally driven via the shaft 11S.

Figure 7:
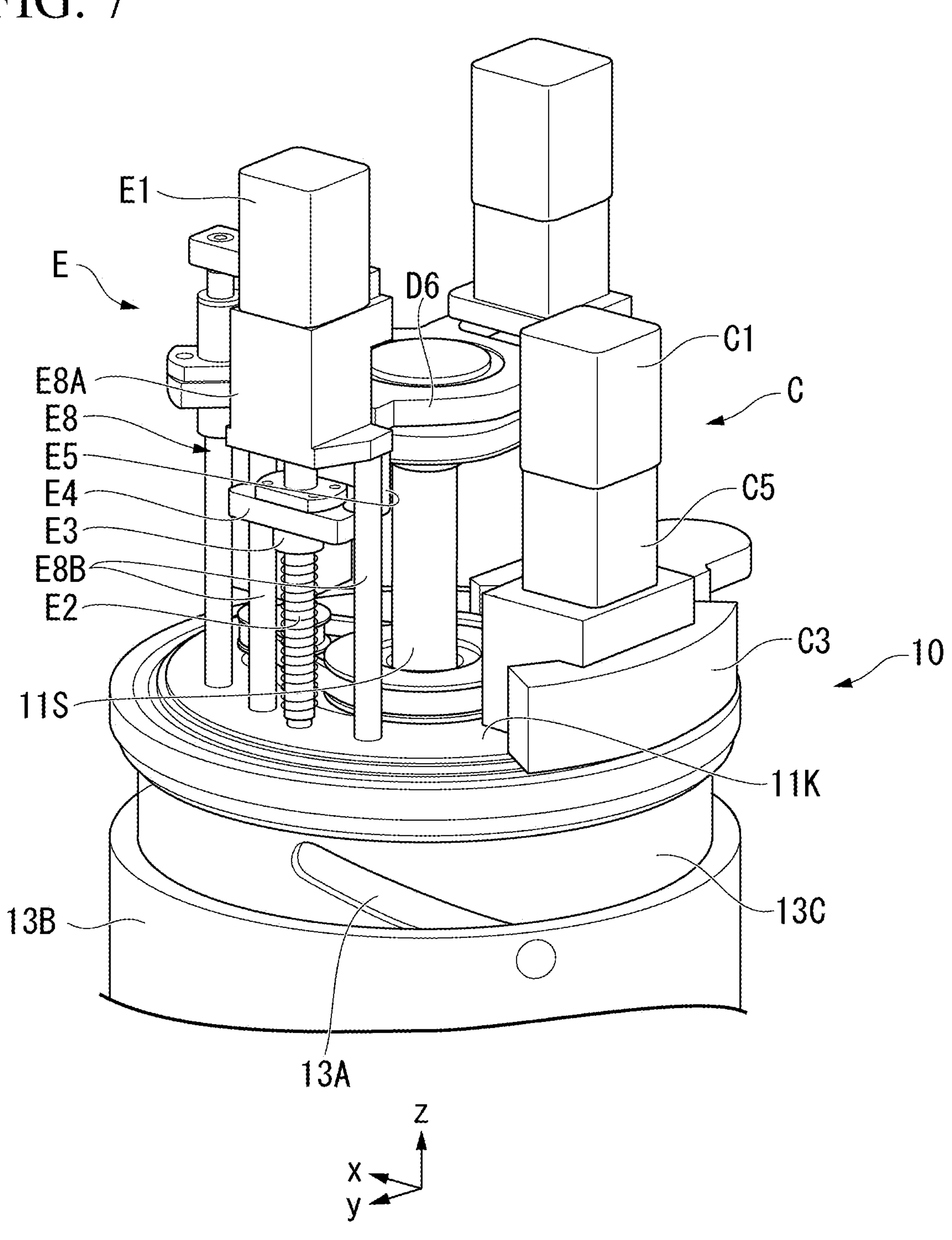
FIG. 7 A perspective view showing a constitution of a third driving unit.

As shown in FIG. 7, the first sonication unit 11B (refer to FIG. 4B) is constituted to be movable along the direction of the central axis L via the shaft 11S by a third driving unit E. The third driving unit E is composed of, for example, a third motor El which serves as a driving source, a support unit E8 which supports the third motor E1, a ball screw E2 which is rotationally driven by the third motor E1, a slide nut E3 which is screwed into the ball screw E2, a base E4 which supports the slide nut E3, and a joint member E5 which joins the base E4 and a support member D6 which supports the second motor D1.

The third motor E1 is fixed to the base unit 11K by the support unit E8. The support unit E8 includes, for example, a fixture member E8A which fixes the third motor E1. The fixture member E8A is fixed to the base unit 11K by two pillars E8B. The third motor E1 includes a rotation shaft (not shown in the drawings) along the central axis L and a ball screw E2 is joined to a lower part of the rotation shaft. The ball screw E2 has a thread groove formed therein. A lower end side of the ball screw E2 is rotatably supported by the base unit 11K via a bearing EB.

A slide nut E3 is screwed onto the ball screw E2. A female thread (not shown in the drawings) into which the thread groove of the ball screw E2 is screwed is formed on the slide nut E3. The slide nut E3 is supported by the base E4. The base E4 is fixed to a support member D6 via the joint member E5. The base E4 is positioned via the support member D6 and the shaft 11S. The rotation of the base E4 around the rotation shaft of the ball screw E2 is regulated by the support member D6 and the shaft 11S. With the above constitution, when the third motor E1 is driven, the ball screw E2 is rotationally driven.

If the ball screw E2 rotates in a predetermined direction around the rotation shaft, for example, the slide nut E3 moves downward. When the slide nut E3 moves downward, the shaft 11S moves downward via the base E4, the joint member E5, and the support member D6. Thus, the second sonication unit 11C moves downward. If the ball screw E2 rotates around the rotation shaft in a direction opposite to a predetermined direction, for example, the slide nut E3 moves upward. If the slide nut E3 moves upward, the shaft 11S moves upward via the base E4, the joint member E5, and the support member D6. Thus, the second sonication unit 11C moves upward.

Figure 8:
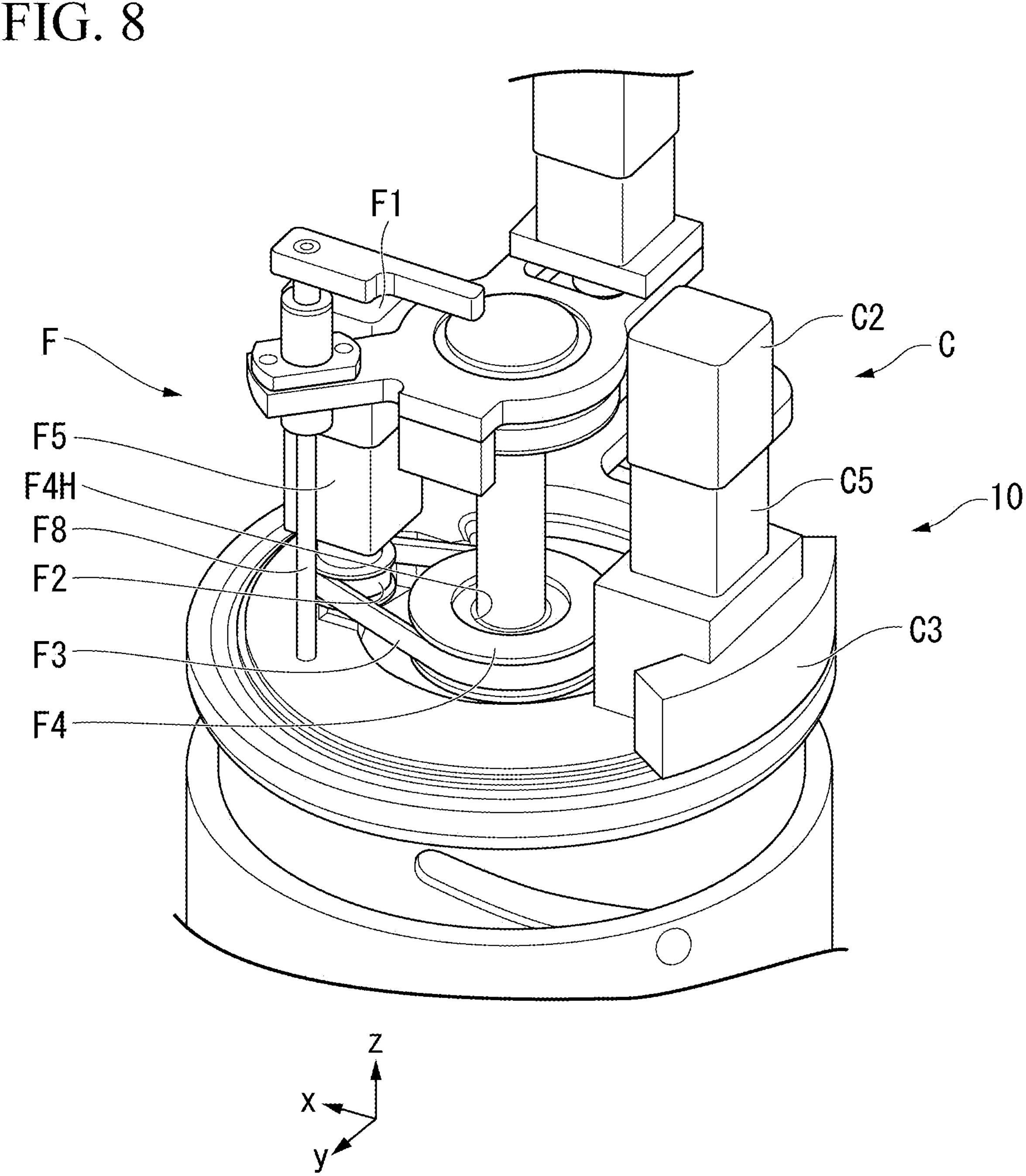
FIG. 8 A perspective view showing a constitution of a fourth driving unit.

FIG. 8 shows a fourth driving unit F which rotationally drives the first sonication unit 11B (refer to FIG. 3 and FIG. 4B) around the central axis L. The first sonication unit 11B is constituted to be rotatable around the central axis L by a fourth driving unit F. The fourth driving unit F is composed of, for example, a fourth motor F1 which serves as a driving source, a third pulley F2 which is rotationally driven by the fourth motor F1, a second belt F3 which transmits rotational power to the third pulley F2, and a fourth pulley F4 which is rotationally driven by the second belt F3. Between the fourth motor F1 and the third pulley F2, a speed reducer F5 which reduces a rotation speed of the fourth motor F1 and increases the torque of the rotation output is provided. If a sufficient torque of the fourth motor F1 is provided, the speed reducer F5 does not necessarily need to be provided. The fourth motor F1 includes a rotation shaft (not shown in the drawings) along the central axis L and the third pulley F2 is provided below the rotation shaft.

For example, the second belt F3 is fitted to the third pulley F2. The fourth pulley F4 is formed to have a diameter larger than that of the third pulley F2. The fourth pulley F4 is fitted to the second belt F3. A through hole F4H is provided in a center of the fourth pulley F4 and the shaft 11S passes through the through hole F4H. A first sonication unit 11B is provided on a side of the lower surface of the fourth pulley F4 to be rotatable about the direction of the central axis L. The fourth motor F1 is fixed to the speed reducer F5. The speed reducer F5 is fixed to the base unit 11K side by the support unit F8. The fourth pulley F4 increases the torque of the rotation output of the third pulley F2 and rotationally drives the first sonication unit 11B. With the above constitution, when the third pulley F2 is rotationally driven by the fourth motor F1, the fourth pulley F4 is rotated via the second belt F3 and the first sonication unit 11B is rotationally driven. When the first sonication unit 11B has "n" focal points X (refer to FIG. 3), a rotationable range only needs to be at least 360°/n (360°/n in one direction or 180°/n in both directions). When the first sonication unit 11B has one focal point X, the first sonication unit 11B does not need to be rotationally driven. When the first sonication unit 11B generates a plurality of focal points X on a plane which is orthogonal to the central axis L, the second sonication unit 11C rotates when determining the position and posture, so the focal points X of the first sonication unit 11B may not coincide with the imaging plane of the second sonication unit 11C. Since the second sonication unit 11C rotates at the time of determining a position and a posture thereof, the focal point X of the first sonication unit 11B and an imaging plane of the second sonication unit 11C may not match in some cases. Since a therapy using ultrasonic waves is localized, there is a concern concerning that, when the focal point X and the imaging plane do not match, a therapy situation cannot be accurately imaged and a therapy accuracy is reduced. For this reason, matching any of a plurality of focal points X and the imaging plane is required. Since a focal point to match may be any focal point, a range in which the first sonication unit 11B can rotate may be the range as described above.

Figure 9:
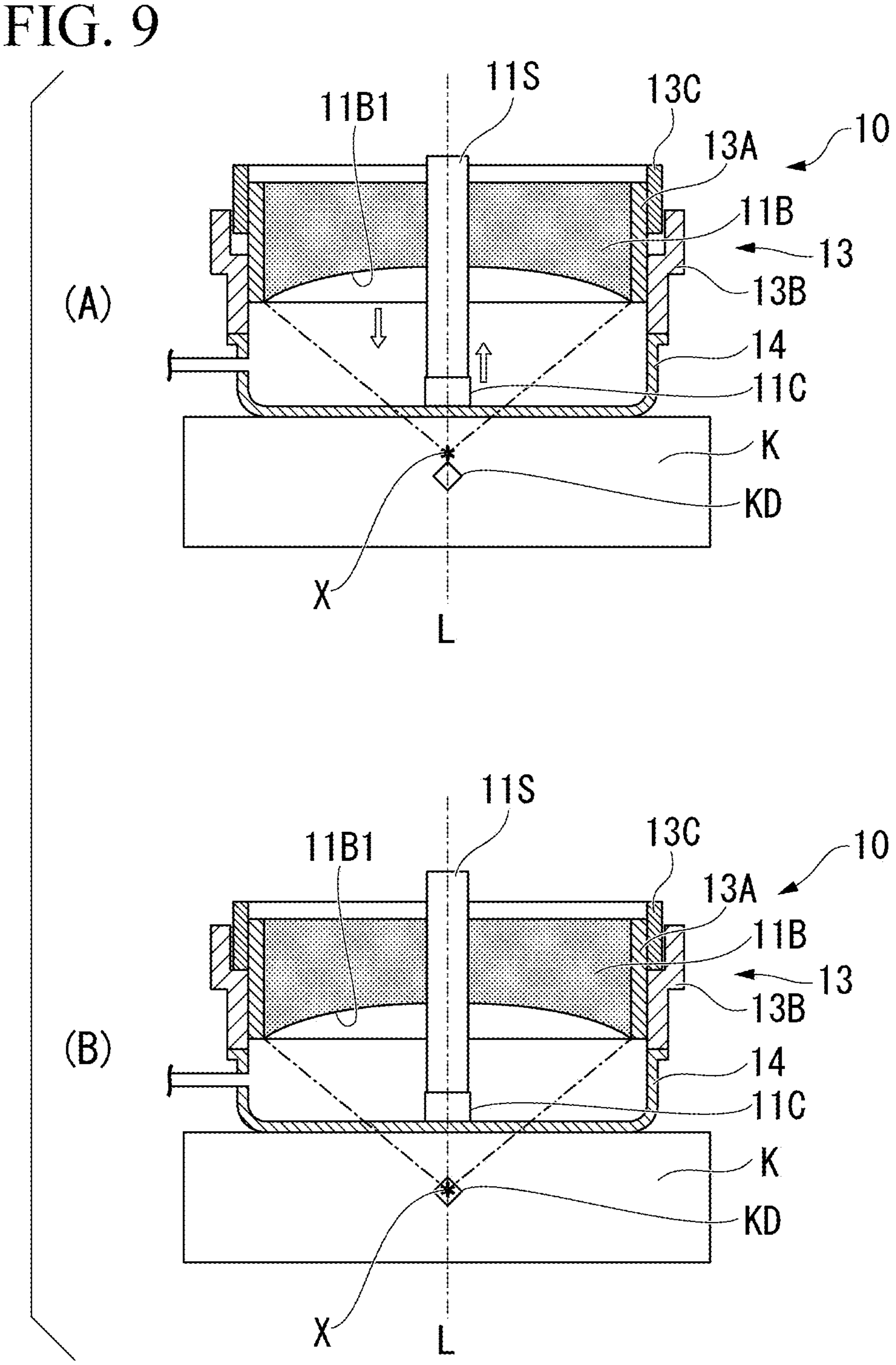
FIG. 9 A cross-sectional view showing an operation of a moving mechanism.

As shown in FIG. 9, an affected part KD exists inside a patient K's body. The second sonication unit 11C comes into contact with an inner wall of the liquid bag 14 and comes into contact with the patient K's body surface through the liquid bag 14. When the focal point X of the ultrasonic waves generated by the sonication surface 11B1 of the first sonication unit 11B is located above the affected part KD (refer to FIG. 9(A)), the second sonication unit 11C is elevated and the operator operates the robot arm 2 to move the ultrasonic head device 10 downward. Thus, the position of the focal point X and the position of the affected part KD can be caused to match (refer to FIG. 9(B)). At this time, there is a concern concerning that the liquid pressure of the medium liquid filled in the liquid storage unit 12 becomes higher than a specified value. Then, the fluid circuit unit 25 discharges the medium liquid in the liquid bag 14, causing the third cylindrical unit 13C to rotate in the moving mechanism 13 and causing the second cylindrical unit 13B to be elevated relative to the first cylindrical unit 13A. Thus, it is possible to bring the liquid bag 14 into contact with the body surface of the patient K while maintaining a water amount and a liquid pressure of the medium liquid in the liquid storage unit 12 at appropriate levels. As a result, ultrasonic waves used for a therapy can be appropriately transmitted from the ultrasonic head device 10 to the affected part via the medium liquid.

Figure 10:
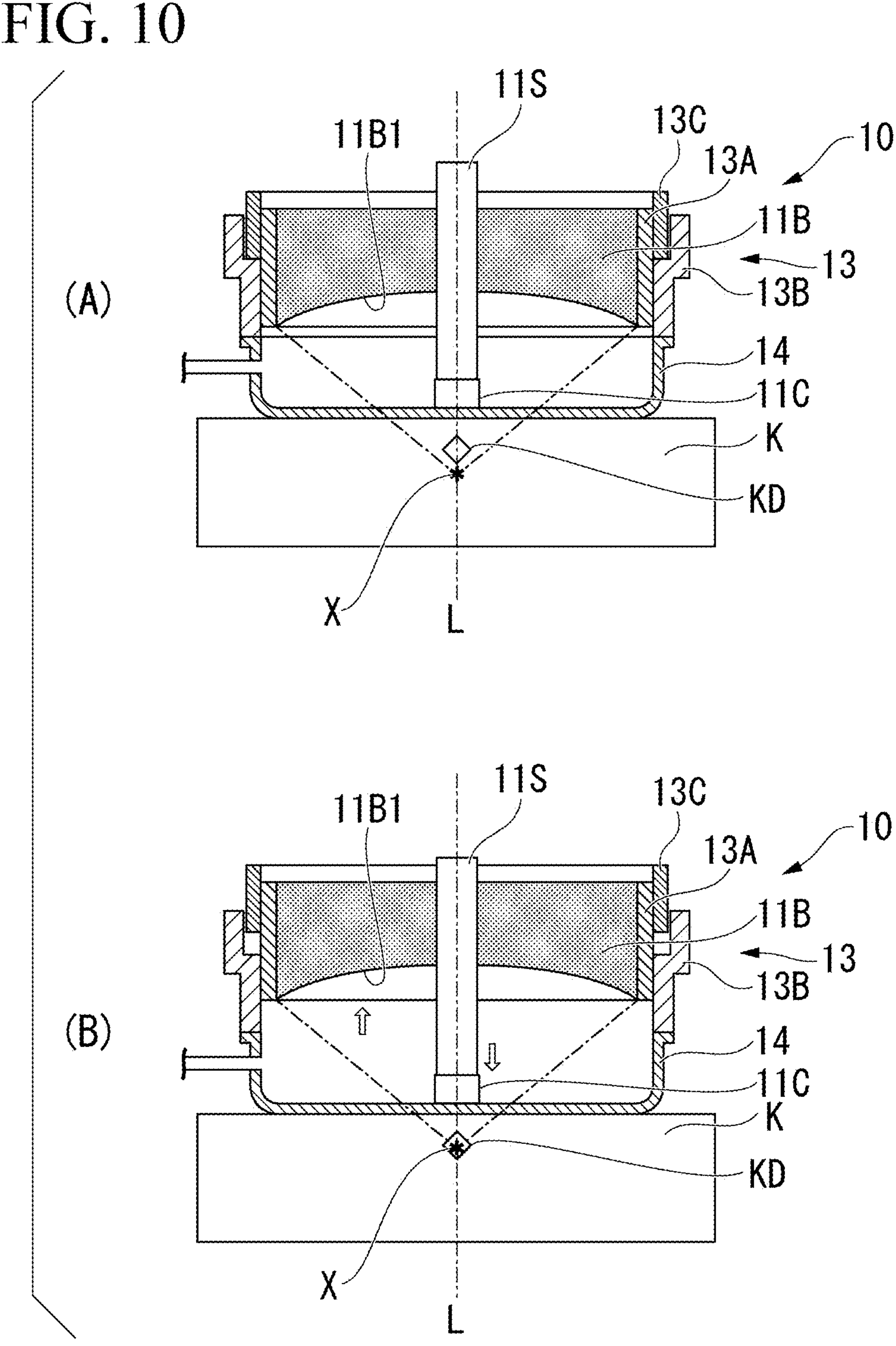
FIG. 10 A cross-sectional view showing an operation of a moving mechanism.

As shown in FIG. 10, an affected part KD exists inside a patient K's body. The second sonication unit 11C comes into contact with an inner wall of the liquid bag 14 and with the patient K's body surface through the liquid bag 14. When the focal point X of the ultrasonic waves generated by the first sonication unit 11B is located below the affected part KD (refer to FIG. 10(A)), the operator operates the robot arm 2 to move the ultrasonic head device 10 upward. After that, the second sonication unit 11C is lowered and brought into contact with the patient K's body surface via the liquid bag 14. Thus, a position of the focal point X and a position of the affected part KD can be caused to match (refer to FIG. 10(B)). At this time, when an insufficient amount of medium liquid filled into the liquid storage unit 12 is provided, the liquid bag 14 cannot maintain an appropriate liquid pressure and there is a concern concerning that air get in between the liquid bag 14 and the patient K's body surface, creating a gap. Furthermore, there is a concern concerning that a contact area between the liquid bag 14 and the patient K is not sufficiently secured and the ultrasonic waves may not be transmitted properly. Then, the fluid circuit unit 25 supplies a medium liquid into the liquid bag 14, causing the third cylindrical unit 13C to rotate in the moving mechanism 13 and causing the second cylindrical unit 13B to be lowered relative to the first cylindrical unit 13A. Thus, it is possible to bring the liquid bag 14 into contact with the patient K's body surface while maintaining a water amount and a liquid pressure of the medium liquid in the liquid storage unit 12 at appropriate levels and it is possible to transmit ultrasonic waves appropriately to the affected part KD. Therefore, cauterization of an unintended place due to improper transmission of ultrasonic waves is prevented.

As described above, the ultrasonic head device 10 can adjust a distance of the liquid bag 14 from the sonication surface 11B1 and a water amount of medium liquid filled in the liquid bag 14 in accordance with a position of the affected part KD from the patient's body surface. Thus, it is possible to maintain a liquid pressure in the liquid bag 14 and a contact surface between the liquid bag 14 and the patient's body surface at appropriate levels. As a result, ultrasonic waves used for a therapy can be appropriately transmitted from the ultrasonic head device 10 to the affected part via the medium liquid. Here, the supply and discharge of the medium liquid by the fluid circuit unit 25 may be performed before or after the moving operation of the moving mechanism 13 or may be performed simultaneously with the moving operation.

Figure 11:
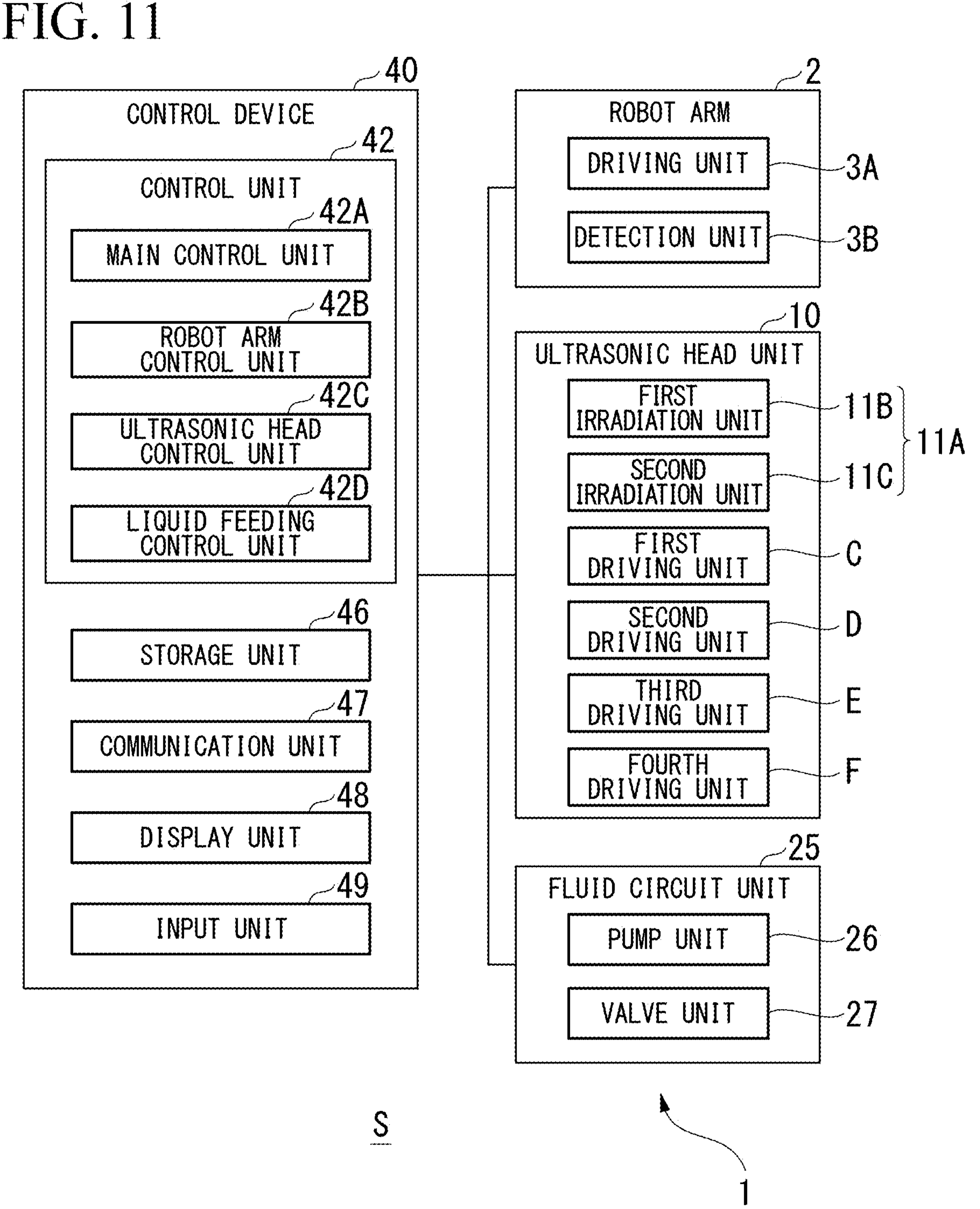
FIG. 11 A block diagram showing a constitution of an ultrasonic therapy system.

FIG. 11 shows a block diagram of a constitution of the ultrasonic therapy system S. The control device 40 controls the ultrasonic therapy device 1 which includes the robot arm 2, the ultrasonic head device 10, and the fluid circuit unit 25. The control device 40 is constituted of, for example, an information processing terminal device such as a personal computer. The control device 40 is communicatively connected to the ultrasonic therapy device 1. The control device 40 may be directly connected to the ultrasonic therapy device 1 or may be a server connected to a network and communicatively connected to the ultrasonic therapy device 1.

The control device 40 includes a control unit 42 which controls the ultrasonic therapy device 1. The control device 40 includes a storage unit 46 in which data necessary for control is stored, a communication unit 47 which communicates with the ultrasonic therapy device 1, a display unit 48 which displays information necessary for control, and an input unit 49 which receives an operation necessary for control.

The storage unit 46 is a data storage device composed of a storage medium such as a hard disk drive or a flash memory. The storage unit 46 may be built into the control device 40 or may be connected externally as an external storage device. The communication unit 47 is a communication interface through which a control signal is transmitted and received to and from the ultrasonic therapy device 1. The communication unit 47 receives an instruction signal requesting control, a detection signal detected from the ultrasonic therapy device 1, or the like and also transmits a control signal for controlling the ultrasonic therapy device 1.

The display unit 48 is composed of a display device such as a liquid crystal display or an organic electro-luminescence (EL) display. The input unit 49 is an information input device such as a touch pad for a keyboard or the like. When the display unit 48 is constituted to be operable through a touch, the input unit 49 may be constituted integrally with the display unit 48. The display unit 48 displays a display image having information regarding the control of the ultrasonic therapy device 1 included therein. The display unit 48 displays a diagnostic image of the patient K's body generated on the basis of a detection value detected by the second sonication unit 11C.

The control unit 42 includes the following plurality of control units for individually controlling the ultrasonic therapy device 1. The control unit 42 includes, for example, a main control unit 42A which generally performs control for the ultrasonic therapy device 1 on the basis of information input from the input unit 49. The control unit 42 includes, for example, a robot arm control unit 42B which controls the robot arm 2 on the basis of an instruction input from the input unit 49. The control unit 42 includes, for example, an ultrasonic head control unit 42C which controls the ultrasonic head device 10 on the basis of an instruction input from the input unit 49. The control unit 42 includes, for example, a liquid feeding control unit 42D which controls the fluid circuit unit 25 on the basis of an instruction input from the input unit 49.

The main control unit 42A generates, for example, an instruction signal for controlling the ultrasonic therapy device 1 on the basis of information input from the input unit 49. The main control unit 42A cooperates with each of the control units described below to perform general control so that the constituent elements of the ultrasonic therapy device 1 operates in cooperation with each other. The main control unit 42A is composed of, for example, a central processing unit provided in the control device 40.

The robot arm control unit 42B controls a driving unit 3A provided on the robot arm 2. The robot arm control unit 42B may be provided, for example, on the robot arm 2 side or may be integrated into the control unit 42 of the control device 40. The robot arm control unit 42B, for example, controls a plurality of driving motors provided at a plurality of joints included in the robot arm 2 respectively. The robot arm control unit 42B acquires an instruction signal requesting the robot arm 2 perform a specific operation, calculates the individual control amounts of the plurality of driving motors on the basis of the details of the instruction signal, and generates a control signal. The robot arm control unit 42B is provided in the driving unit 3A and acquires detection data from a detection unit 3B which detects a rotation angle, torque, or the like of each of the driving motors. The robot arm control unit 42B generates a control signal according to a posture of the plurality of arm members 3-*n* and the magnitude and a direction of an action force to be applied on the basis of the data acquired from the detection unit 3B and controls the robot arm 2. Furthermore, the robot arm 2 may be a collaborative robot. In this case, when the operator applies a force to change the posture of the robot arm 2, the robot arm control unit 42B controls the plurality of driving motors respectively to change the position and the posture of the ultrasonic head device 10 in accordance with the operator's operation.

The robot arm control unit 42B transmits a control signal to the robot arm 2 via the communication unit 47 to perform control so that the robot arm 2 performs a predetermined operation. The robot arm control unit 42B acquires data regarding a driving amount of each of the joints of the robot arm 2 via the communication unit 47 and adjusts an operation of the robot arm 2.

The robot arm control unit 42B controls the robot arm 2, for example, during a therapy and performs positioning so that the focal point X of the first sonication unit 11B of the ultrasonic head device 10 provided on the robot arm 2 is placed at a position of the affected part KD of the patient K and holds it to have a predetermined posture. The robot arm control unit 42B, for example, controls the robot arm 2 as described later during preparation for another therapy after a therapy is completed and holds the ultrasonic head device 10 to have a predetermined first posture so that a medium liquid is easily discharged from the liquid storage unit 12 of the ultrasonic head device 10. The robot arm control unit 42B, for example, controls the robot arm 2 as described later during preparation for a therapy before the therapy begins and holds the ultrasonic head device 10 to have a predetermined second posture so that a medium liquid is easily supplied to the liquid storage unit 12 of the ultrasonic head device 10.

During a therapy, after the ultrasonic head device 10 is positioned at a predetermined position, the ultrasonic head control unit 42C controls the ultrasonic head device 10 on the basis of the acquired instruction signal to perform the required operations. The ultrasonic head control unit 42C, for example, may be provided on the ultrasonic head device 10 side or may be integrated into the control unit 42 of the control device 40. The ultrasonic head control unit 42C acquires an instruction signal requesting a predetermined operation from the ultrasonic head device 10, calculates individual control amounts of the plurality of sonication units on the basis of the details of the instruction signal, and generates a control signal. The ultrasonic head control unit 42C transmits a control signal to the ultrasonic head device 10 via the communication unit 47 and controls the ultrasonic head device 10 so that the ultrasonic head device 10 performs a necessary operation. The ultrasonic head control unit 42C controls, for example, the first driving unit C to rotate the third cylindrical unit 13C and adjust an amount of movement along the axial direction of the second cylindrical unit 13B, thereby controlling a position of the liquid bag 14 from the sonication surface 11B1.

Also, the ultrasonic head control unit 42C controls the fourth driving unit F to rotate the first sonication unit 11B around the central axis L so that any of the plurality of focal points X of the therapeutic ultrasonic waves and a scanning plane of the second sonication unit 11C match. The ultrasonic head control unit 42C controls the third driving unit E to adjust an amount of movement of the shaft 11S and bring the second sonication unit 11C into contact with an inner wall of the liquid bag 14. The ultrasonic head control unit 42C controls the second driving unit D to rotate the second sonication unit 11C around the central axis L and adjust a scanning direction of the diagnostic ultrasound to the affected part KD.

The liquid feeding control unit 42D controls a plurality of circuit control instruments composed of a pump unit 26 and a valve unit 27 provided in the fluid circuit unit 25 to circulate a medium liquid through the fluid circuit unit 25. The fluid circuit unit 25 is constituted as a liquid supplying and discharging mechanism which supplies a medium liquid to the liquid bag 14 and discharges the medium liquid from the liquid bag 14. When supplying a medium liquid into the liquid bag 14, the liquid feeding control unit 42D controls the pump unit 26 and the valve unit 27 to cause the medium liquid to flow from the fluid circuit unit 25 into the liquid bag 14 via an inflow connection unit 14RA. When discharging the medium liquid from the liquid bag 14, the liquid feeding control unit 42D controls the pump unit 26 and the valve unit 27 to discharge the medium liquid from the liquid bag 14 to the fluid circuit unit 25 via a discharge connection unit 14RB.

The liquid feeding control unit 42D cooperates with the ultrasonic head control unit 42C to control the fluid circuit unit 25. When the ultrasonic head control unit 42C controls the moving mechanism to move the liquid bag, the liquid feeding control unit 42D controls the liquid supplying and discharging mechanism so that the internal space of the liquid bag 14 which changes in response to the movement is filled with the medium liquid. The liquid feeding control unit 42D may be provided on the housing 20 side or may be integrated into the control unit 42 of the control device 40. The liquid feeding control unit 42D acquires an instruction signal requesting a predetermined operation from the plurality of circuit control instruments, calculates individual control amounts for the plurality of circuit control instruments on the basis of the details of the instruction signal, and generates a control signal. The liquid feeding control unit 42D transmits a control signal to the plurality of circuit control instruments via the communication unit 47 and controls the plurality of circuit control instruments to perform a necessary operation.

During a therapy, the liquid feeding control unit 42D controls the fluid circuit unit 25 to adjust an amount of medium liquid stored in the liquid storage unit 12. When the ultrasonic head device 10 is held to have a predetermined first posture during preparation for another therapy after a therapy has been completed, the liquid feeding control unit 42D controls the fluid circuit unit 25 to discharge a medium liquid from the liquid storage unit 12 and discharges the medium liquid from the fluid circuit unit 25. During preparation for a therapy before the therapy begins, when the ultrasonic head device 10 is held to have a predetermined second posture, the liquid feeding control unit 42D controls the fluid circuit unit 25 to supply a new medium liquid to the fluid circuit unit 25 and supply a medium liquid to the liquid storage unit 12. With the above constitution, the control device 40 can operate the ultrasonic therapy device 1 in an integrated manner on the basis of the input operation details.

These constituent elements which constitute the control unit 42 described above including the main control unit 42A, the robot arm control unit 42B, the ultrasonic head control unit 42C, and the liquid feeding control unit 42D are realized, for example, by a hardware processor such as a Central Processing Unit (CPU) executing a program (software). Some or all of these constituent elements may be realized by hardware (circuit unit; including a circuitry) such as a Large Scale Integration (LSI), an Application Specific Integrated Circuit (ASIC), a Field-Programmable Gate Array (FPGA), or a Graphics Processing Unit (GPU) or may be realized through a combination of software and hardware. The program may be stored in advance in a storage device (storage device including a non-transient storage medium) such as a hard disk drive (HDD) or a flash memory, or may be stored on a removable storage medium (non-transient storage medium) such as a DVD or a CD-ROM and installed by inserting the storage medium into the drive device. The process performed in the control unit 42 may be performed by a computer on a server through cloud computing. The function of the process performed in the control unit 42 may be performed in a distributed manner in a plurality of distributed computers.

Figure 12:
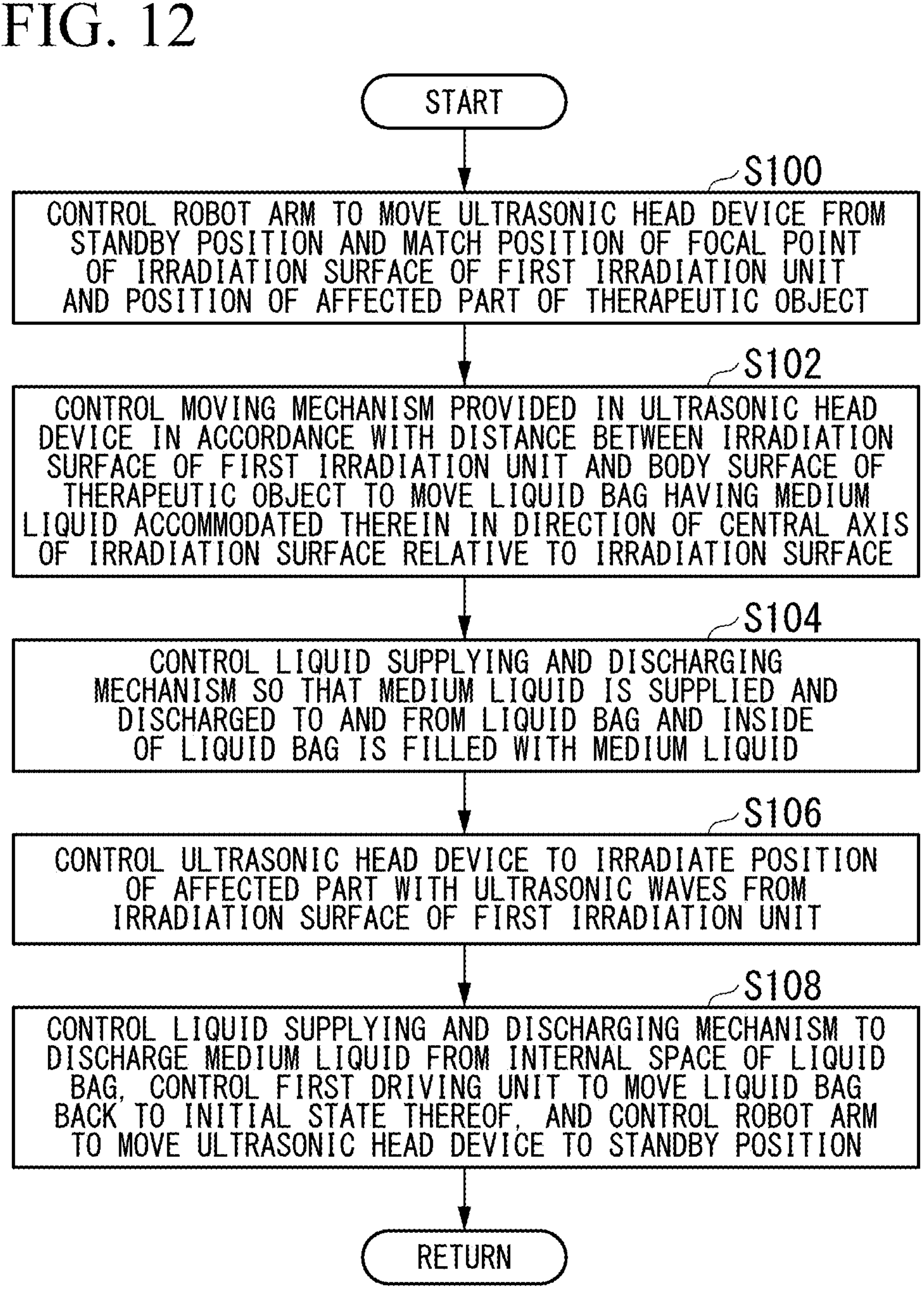
FIG. 12 A flowchart for describing a method for controlling an ultrasonic therapy system.

FIG. 12 shows a flow of a process of a control method performed in the ultrasonic therapy system S. In the control device 40, the robot arm control unit 42B controls the robot arm 2 to move the ultrasonic head device 10 supported by the robot arm 2 from the standby position (movement step) and matches a position of a focal point X of the sonication surface 11B1 of the first sonication unit 11B and a position of an affected part of a therapeutic object (alignment step) (Step S100). The ultrasonic head control unit 42C controls the moving mechanism 13 provided in the ultrasonic head device 10 in accordance with a distance between the sonication surface 11B1 of the first sonication unit 11B and a body surface of the therapeutic object to move the liquid bag 14 having a medium liquid accommodated therein along the direction of the central axis of the sonication surface 11B1 relative to the sonication surface 11B1 (first movement step) (Step S102).

The liquid feeding control unit 42D controls the liquid supplying and discharging mechanism so that the medium liquid is circulated through the liquid bag and the medium liquid is supplied into the liquid bag (supply step) (Step S104). The ultrasonic head control unit 42C controls the ultrasonic head device to sonicate the position of the affected part with ultrasonic waves from the sonication surface 11B1 of the first sonication unit 11B (sonication step) (Step S106). The control unit 42 controls the liquid supplying and discharging mechanism to discharge the medium liquid from the internal space of the liquid bag 14 (discharge step), controls the first driving unit to move the liquid bag 14 back to an initial state thereof (second movement step), and controls the robot arm 2 to move the ultrasonic head device 10 to a standby position (Step S108). Furthermore, the control unit 42 may control the robot arm 2 to move the ultrasonic head device 10 to the standby position, then control the liquid supplying and discharging mechanism to discharge the medium liquid from an internal space of the liquid bag 14, and control the first driving unit to move the liquid bag 14 back to an initial state thereof. The above steps may be interchanged or may be performed simultaneously.

As described above, according to the ultrasonic therapy device 1, by changing the position and the posture of the ultrasonic head device 10 by operating the robot arm 2, the position of the focal point X of an HIFU radiated for sonication by the first sonication unit 11B can be adjusted to a position of the affected part KD. According to the ultrasonic head device 10, the liquid bag 14 can be moved in the axial direction by the moving mechanism 13 so that the volume and the liquid pressure of the liquid storage unit 12 can be set to appropriate values in accordance with the distance between the sonication surface 11B1 of the first sonication unit 11B and the body surface of the patient K. As a result, ultrasonic waves used for a therapy can be appropriately transmitted from the ultrasonic head device 10 to the affected part via the medium liquid.

The moving mechanism 13 is constituted so that the second cylindrical unit 13B moves relative to the first cylindrical unit 13A and the liquid bag 14 is formed to have a bowl shape in which it bulges downward, thereby preventing air bubbles from getting into the medium liquid when an inside of the liquid bag 14 is filled with the medium liquid. According to the ultrasonic head device 10, by reducing the angle between the second groove portion 13CM formed in the third cylindrical unit 13C and the plane perpendicular to the central axis L, the force required for rotationally driving the second cylindrical unit 13B can be reduced, and the first driving unit C and the device constitution can be made smaller.

MODIFIED EXAMPLE

A modified example of the moving mechanism 13 is explained below. In the following description, the same constituent elements as those of the above embodiments are denoted by the same names and reference signs and duplicated description thereof is omitted as appropriate.

Figure 13:
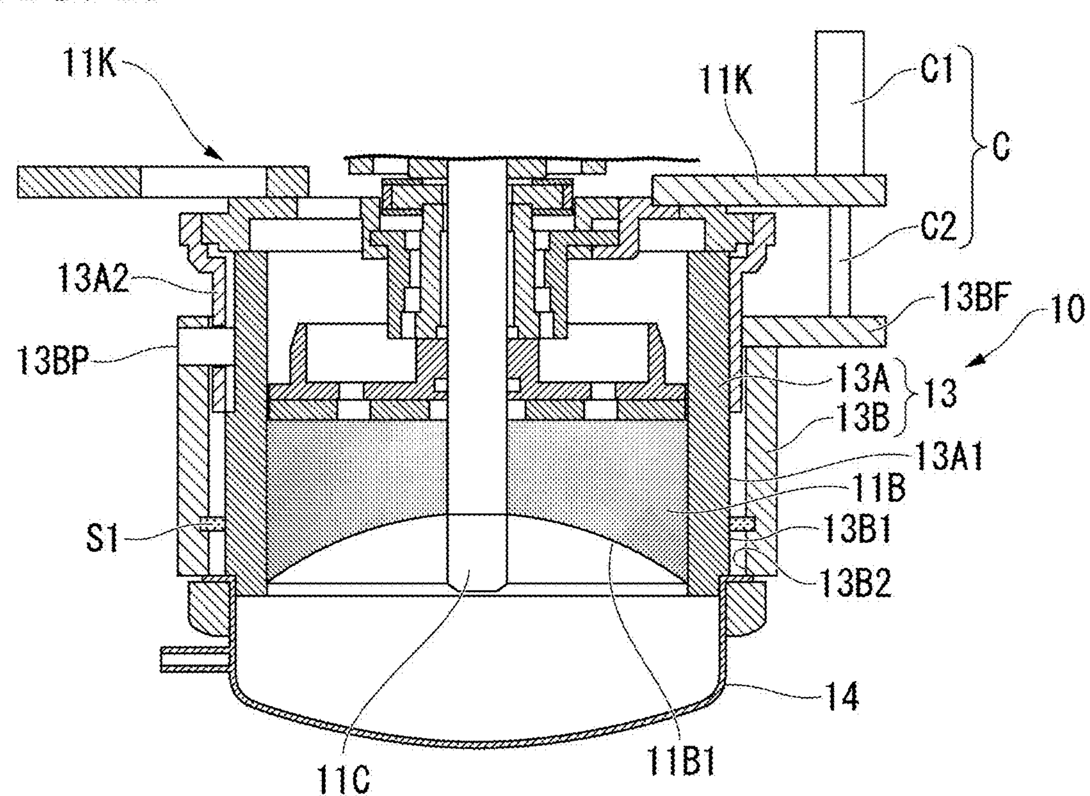
FIG. 13 A cross-sectional view showing a constitution of a moving mechanism according to a modified example.

As shown in FIG. 13, the moving mechanism 13 may be driven by the first driving unit C provided on the base unit 11K formed to protrude in the outer circumferential direction of the ultrasonic head device 10. The first driving unit C is constituted of a linear driving device such as an electric cylinder or an air cylinder. The first driving unit C has a cylinder body serving as a driving source C1 and a rod serving as an output unit C2. The first driving unit C has a cylinder main body provided to be fixed to the base unit 11K. In addition, in a plan view, a rod and a fixture unit of the second cylindrical unit flange 13BF described later are positioned further outward than the outer circumferential surface 13B1 of the second cylindrical unit 13B. The rod extends in the axial direction and a lower end portion thereof is fixed to a second cylindrical unit flange 13BF provided in the second cylindrical unit 13B. By extending and retracting the rod in the axial direction, the second cylindrical unit 13B can be moved relative to the first cylindrical unit 13A. At this time, the second cylindrical unit 13B is constituted to move within a predetermined range of an amount of movement in the axial direction relative to the first cylindrical unit 13A. Furthermore, in the modified example, as in the above embodiments, one or more first groove portions 13A2 may be formed on the outer circumferential surface 13A1 of the first cylindrical unit 13A along the direction of the central axis of the first cylindrical unit 13A and the second cylindrical unit 13B may include one or more engagement members 13BP which protrude inward in the radial direction from the inner radial surface of the second cylindrical unit 13B, and are formed to be engaged with the first groove portions 13A2. In addition, one or more first groove portions (not shown in the drawings) may be formed on the inner circumferential surface 13B2 of the second cylindrical unit 13B along the direction of the central axis of the second cylindrical unit 13B and the first cylindrical unit 13A may include one or more engagement members (not shown in the drawings) which protrude outward in the radial direction from the outer radial surface of the first cylindrical unit 13A, and are formed to be engaged with the first groove portions (not shown in the drawings). In the moving mechanism 13 according to the modified example in this case, the third cylindrical unit 13C may be omitted.

Although one embodiment of the present invention is described above, the present invention is not limited to the above embodiment and can be modified as appropriate without departing from the spirit of the present invention.

REFERENCE SIGNS LIST

2 Robot arm
3A Driving unit
10 Ultrasonic head device
11A Sonication unit
11B First sonication unit
11B1 Sonication surface
11C Second sonication unit
11K Base unit
13 Moving mechanism
13A First cylindrical unit
13A1 Outer circumferential surface
13A2 First groove portion
13A3 Sliding region
13B Second cylindrical unit
13B1 Outer circumferential surface
13BP Engagement member
13C Third cylindrical unit
13C2 Cylindrical unit
13CF Flange unit
13CM Second groove portion
14 Liquid bag
14C Flange unit
14R Liquid supplying and discharging unit
40 Control device
C First driving unit
C1 Driving source
C2 Output unit
D Second driving unit
E Third driving unit
F Fourth driving unit
KD Affected part
L Central axis
S Ultrasonic therapy system
T Attachment unit
X Focal point

The invention claimed is:

1. An ultrasonic head device supported by a robot arm which is able to be held in any posture state, the ultrasonic head device being applied to an ultrasonic therapy system which sonicates an inside of a therapeutic object with ultrasonic waves, the ultrasonic head device comprising:

a base unit which is supported by the robot arm;

a sonication unit which provided on the base unit and includes a hemispherical sonication surface configured to radiate the ultrasonic waves for sonication;

a liquid bag which has a medium liquid through which the ultrasonic waves are transmitted accommodated therein and with which the sonication surface is covered;

a liquid supplying and discharging unit which circulates the medium liquid through the liquid bag; and a moving mechanism which is provided on the base unit and supports the liquid bag so that the liquid bag can be freely moved relative to the sonication surface along a direction of a central axis of the sonication surface, wherein the moving mechanism includes:

a first cylindrical unit which is provided on a side of the base unit;

a second cylindrical unit which is provided to be freely moved relative to the first cylindrical unit along the direction of the central axis; and a first driving unit which moves the second cylindrical unit along the direction of the central axis, and the second cylindrical unit has the liquid bag fixed on a side which is different from the side of the base unit along the direction of the central axis.

2. The ultrasonic head device according to claim 1, wherein one or more first groove portions are formed along the direction of the central axis in one of the first cylindrical unit and the second cylindrical unit, and one or more engagement members which protrude in a radial direction and are formed to be engaged with the one or more first groove portions are provided in the other of the first cylindrical unit and the second cylindrical unit.

3. The ultrasonic head device according to claim 2, wherein one of the first cylindrical unit and the second cylindrical unit is inserted into the other thereof, the moving mechanism includes a third cylindrical unit disposed between the first cylindrical unit and the second cylindrical unit in a radial direction, the first cylindrical unit includes the one or more first groove portions, the second cylindrical unit includes the engagement members, one or more second groove portions which are inclined with respect to the direction of the central axis and through which the engagement members pass through are formed to extend in a circumferential direction of the third cylindrical unit with respect to the central axis, and the first driving unit rotates the third cylindrical unit using the central axis as a rotation shaft, and the third cylindrical unit is rotationally driven in the circumferential direction with respect to the first cylindrical unit and the second cylindrical unit, so that the engagement members move relatively along the one or more second groove portions and the one or more first groove portions, and the second cylindrical unit is moved in a direction along the direction of the central axis with respect to the first cylindrical unit on the basis of a rotation direction.

4. The ultrasonic head device according to claim 1, wherein a sealing unit which seals a gap and formed along a circumferential direction is provided between the first cylindrical unit and the second cylindrical unit, the first cylindrical unit includes a sealed portion which is sealed by the sealing unit, and the second cylindrical unit includes a sealing groove portion having the sealing unit disposed therein.

5. The ultrasonic head device according to claim 4, wherein the second cylindrical unit includes an attachment unit which allows the liquid bag to be freely attachable to and detachable from a lower portion of the second cylindrical unit, and the attachment unit includes an annular member which is freely attachable and detachable at a lower end of the second cylindrical unit.

6. The ultrasonic head device according to claim 5, wherein the liquid bag is constituted to have a hemispherical shape in which the liquid bag includes an end portion having a flange unit provided thereon, and the annular member is engaged with the flange unit and cooperates with a lower end of the second cylindrical unit so that the annular member and the lower end have the flange unit placed therebetween.

7. The ultrasonic head device according to claim 6, wherein the sonication unit includes:

a first sonication unit which includes the sonication surface and sonicates an affected part of the therapeutic object with ultrasonic waves to treat the affected part; and a second sonication unit which protrudes from the sonication surface and scans the therapeutic object with ultrasonic waves to generate cross-sectional images, and the ultrasonic head device further comprises:

a second driving unit which rotationally drives the first sonication unit about the central axis;

a third driving unit which rotationally drives the second sonication unit about the central axis; and a fourth driving unit which moves the second sonication unit in a direction along the central axis.

8. An ultrasonic therapy system, comprising:

an ultrasonic head device which sonicates an inside of a therapeutic object with ultrasonic waves;

a robot arm which is able to hold the ultrasonic head device in any posture state;

a liquid supplying and discharging mechanism which is connected to the ultrasonic head device; and a control device which controls the ultrasonic head device and the liquid supplying and discharging mechanism, wherein the ultrasonic head device includes:

a base unit which is supported by the robot arm;

a sonication unit which is provided on the base unit and includes a sonication surface which radiates the ultrasonic waves for sonication;

a liquid bag which has a medium liquid through which the ultrasonic waves are transmitted accommodated therein and with which the sonication surface is covered;

a liquid supplying and discharging unit which circulates the medium liquid through the liquid bag; and a moving mechanism which is provided on the base unit and supports the liquid bag so that the liquid bag is freely moved relative to the sonication surface along a direction of a central axis of the sonication surface, the moving mechanism includes:

a first cylindrical unit provided on a side of the base unit;

a second cylindrical unit which is provided to be freely moved along the direction of the central axis with respect to the first cylindrical unit and includes a lower side having the liquid bag fixed thereto; and a first driving unit which moves the second cylindrical unit relative to the first cylindrical unit, and the liquid supplying and discharging mechanism supplies the medium liquid to the liquid supplying and discharging unit or discharges the medium liquid from the liquid supplying and discharging unit.

9. The ultrasonic therapy system according to claim 8, wherein the control device controls the moving mechanism to move the liquid bag, and the control unit controls the liquid supplying and discharging mechanism to supply the medium liquid to or discharge the medium liquid from an internal space of the liquid bag which changes in accordance with movement.

10. A method for controlling an ultrasonic therapy system, the system including:

an ultrasonic head device by which an inside of a therapeutic object is sonicated with ultrasonic waves;

a robot arm which is able to hold the ultrasonic head device in any posture state;

a liquid supplying and discharging mechanism by which a medium liquid through which the ultrasonic waves are transmitted to the ultrasonic head device is supplied or discharged; and a control device which controls the ultrasonic head device, the robot arm, and the liquid supplying and discharging mechanism, the method comprising:

a process performed by the control device and including:

a movement step of controlling the robot arm to move the ultrasonic head device supported by the robot arm;

an alignment step of matching a position of a focal point of a sonication surface which is provided on the ultrasonic head device and by which the ultrasonic waves are radiated for sonication and a position of an affected part of a therapeutic object;

a first movement step of controlling a moving mechanism provided on the ultrasonic head device to move a liquid bag which is provided on the ultrasonic head device, with which the sonication surface is covered, and which has the medium liquid accommodated therein relative to the sonication surface along a direction of a central axis of the sonication surface;

a supply step of controlling the liquid supplying and discharging mechanism so that the medium liquid is circulated through the liquid bag and the medium liquid is supplied into the liquid bag; and a sonication step of controlling the ultrasonic head device to sonicate a position of the affected part with the ultrasonic waves from the sonication surface.

11. The method for controlling an ultrasonic therapy system according to claim 10, further comprising:

after the sonication step, a discharge step of controlling the liquid supplying and discharging mechanism to discharge the medium liquid from an internal space of the liquid bag; and a second movement step of controlling the moving mechanism to move the liquid bag relative to the sonication surface along the direction of the central axis of the sonication surface.

* * * * *